(12) United States Patent
Dreher et al.

(10) Patent No.: US 10,828,244 B2
(45) Date of Patent: Nov. 10, 2020

(54) COMPOSITIONS FOR TREATING THE HAIR

(71) Applicant: L'OREAL, Paris (FR)

(72) Inventors: Kimberly Christine Dreher, Old Bridge, NJ (US); Gérard Provot, Saint-Ouen (FR); Dariusz Danielski, Chicago, IL (US); Fabien Pascal Boulineau, Livingston, NJ (US); Caroline Rahmouna Françoise Goget, Summit, NJ (US); Anthony Potin, Hoboken, NJ (US); Allison Chin, Hoboken, NJ (US); Michael Degeorge, Old Bridge, NJ (US); Mara Applebaum, Plainfield, NJ (US); Mary Abraam Soliman, Kendall Park, NJ (US); Ashley Ann Figatner, Lawrenceville, NJ (US); Megan Pauker, South Plainfield, NJ (US); Emmanuel Appiah-Amponsah, Metuchen, NJ (US)

(73) Assignee: L'OREAL, Paris (FR)

( * ) Notice: Subject to any disclaimer, the term of this patent is extended or adjusted under 35 U.S.C. 154(b) by 141 days.

(21) Appl. No.: 15/778,805

(22) PCT Filed: Nov. 24, 2016

(86) PCT No.: PCT/US2016/063732
§ 371 (c)(1),
(2) Date: Nov. 5, 2018

(87) PCT Pub. No.: WO2017/091800
PCT Pub. Date: Jun. 1, 2017

(65) Prior Publication Data
US 2019/0060197 A1 Feb. 28, 2019

Related U.S. Application Data

(60) Provisional application No. 62/259,572, filed on Nov. 24, 2015.

(51) Int. Cl.
| | |
|---|---|
| A61K 8/41 | (2006.01) |
| A61Q 5/08 | (2006.01) |
| A61Q 5/10 | (2006.01) |
| A61Q 5/12 | (2006.01) |
| A61K 8/362 | (2006.01) |
| A61K 8/365 | (2006.01) |
| A61Q 5/00 | (2006.01) |
| A61Q 5/06 | (2006.01) |
| A45D 7/04 | (2006.01) |
| A61K 8/368 | (2006.01) |
| A45D 7/00 | (2006.01) |

(52) U.S. Cl.
CPC ............ *A61K 8/41* (2013.01); *A45D 7/04* (2013.01); *A61K 8/362* (2013.01); *A61K 8/365* (2013.01); *A61K 8/368* (2013.01); *A61Q 5/002* (2013.01); *A61Q 5/065* (2013.01); *A61Q 5/08* (2013.01); *A61Q 5/10* (2013.01); *A61Q 5/12* (2013.01); *A45D 2007/001* (2013.01); *A61K 2800/43* (2013.01); *A61K 2800/88* (2013.01); *A61K 2800/884* (2013.01); *A61Q 5/06* (2013.01)

(58) Field of Classification Search
CPC .. A61K 2800/884; A61K 8/362; A61K 8/365; A61K 8/41; A61K 2800/43; A61K 2800/88; A61K 8/368; A61Q 5/002; A61Q 5/08; A61Q 5/12; A61Q 5/065; A61Q 5/10; A61Q 5/06; A45D 2007/001; A45D 7/04
See application file for complete search history.

(56) References Cited

U.S. PATENT DOCUMENTS

| | | | |
|---|---|---|---|
| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |
| 2,850,351 | A | 9/1958 | Moore et al. |
| 2,961,347 | A | 11/1960 | Floyd |
| 3,142,623 | A | 7/1964 | Zviak et al. |
| 3,193,464 | A | 7/1965 | Edman et al. |
| 3,206,462 | A | 9/1965 | McCarty |
| 3,227,615 | A | 1/1966 | Korden |
| 3,472,243 | A | 10/1969 | Wall et al. |
| 3,472,840 | A | 10/1969 | Stone et al. |

(Continued)

FOREIGN PATENT DOCUMENTS

| | | |
|---|---|---|
| CN | 102451117 A | 5/2012 |
| CN | 105267066 A | 1/2016 |
| CN | 105902403 A | 8/2016 |
| CN | 105902404 A | 8/2016 |
| CN | 106265109 A | 1/2017 |
| DE | 1220969 B | 7/1966 |
| DE | 2225541 A1 | 12/1973 |
| DE | 2359399 A1 | 6/1975 |

(Continued)

OTHER PUBLICATIONS

Supplementarty Extended Search Report and Written Opinion for counterpart European Application No. 16869324, dated Apr. 9, 2019.

(Continued)

*Primary Examiner* — Audrea B Coniglio
(74) *Attorney, Agent, or Firm* — The Marbury Law Group, PLLC

(57) ABSTRACT

The disclosure relates to compositions for treating keratinous substrates, such as the hair, comprising 2-(2-aminoethoxy)ethanol and at least one carboxylic acid, as well as systems and methods for treating keratinous substrates with the compositions.

29 Claims, 5 Drawing Sheets

(56) References Cited

U.S. PATENT DOCUMENTS

| | | |
|---|---|---|
| 3,589,978 A | 6/1971 | Kamal et al. |
| 3,632,559 A | 1/1972 | Matter et al. |
| 3,840,656 A | 10/1974 | Kalopissis et al. |
| 3,874,870 A | 4/1975 | Green et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,412,934 A | 11/1983 | Chung et al. |
| 4,422,853 A | 12/1983 | Jacquet et al. |
| 4,425,132 A | 1/1984 | Grollier et al. |
| 4,532,950 A | 8/1985 | Lang et al. |
| 4,579,732 A | 4/1986 | Grollier et al. |
| 4,591,610 A | 5/1986 | Grollier |
| 4,608,250 A | 8/1986 | Jacquet et al. |
| 4,761,273 A | 8/1988 | Grollier et al. |
| 4,770,873 A | 9/1988 | Wolfram et al. |
| 4,777,040 A | 10/1988 | Grollier et al. |
| 4,793,992 A | 12/1988 | Mathews et al. |
| 4,793,993 A | 12/1988 | Siuta-Mangano et al. |
| 4,812,307 A | 3/1989 | Siuta-Mangano |
| 4,834,971 A | 5/1989 | Klenk et al. |
| 4,906,460 A | 3/1990 | Kim et al. |
| 4,948,579 A | 8/1990 | Jacquet et al. |
| 4,970,066 A | 11/1990 | Grollier et al. |
| 5,061,289 A | 10/1991 | Clausen et al. |
| 5,085,860 A | 2/1992 | Junino et al. |
| 5,143,518 A | 9/1992 | Madrange et al. |
| 5,196,189 A | 3/1993 | Jacquet et al. |
| 5,221,286 A | 6/1993 | Singleton et al. |
| 5,293,885 A | 3/1994 | Darkwa et al. |
| 5,350,572 A | 9/1994 | Savaides et al. |
| 5,356,438 A | 10/1994 | Kim et al. |
| 5,380,340 A | 1/1995 | Neunhoeffer et al. |
| 5,534,267 A | 7/1996 | Neunhoeffer et al. |
| 5,565,216 A | 10/1996 | Cowsar et al. |
| 5,593,662 A | 1/1997 | Deckner et al. |
| 5,616,150 A | 4/1997 | Moeller et al. |
| 5,628,991 A | 5/1997 | Samain et al. |
| 5,635,168 A | 6/1997 | Burns et al. |
| 5,651,960 A | 7/1997 | Chan et al. |
| 5,656,265 A | 8/1997 | Bailey et al. |
| 5,663,366 A | 9/1997 | Neunhoeffer et al. |
| 5,688,291 A | 11/1997 | Said et al. |
| 5,708,151 A | 1/1998 | Mockli |
| 5,766,576 A | 6/1998 | Lowe et al. |
| 5,811,085 A | 9/1998 | Halloran |
| 5,833,966 A | 11/1998 | Samain |
| 5,951,969 A | 9/1999 | Golinski et al. |
| 5,972,322 A | 10/1999 | Rath et al. |
| 5,985,803 A | 11/1999 | Rizvi et al. |
| 6,013,250 A | 1/2000 | Cannell et al. |
| 6,036,966 A | 3/2000 | Youssefyeh |
| 6,099,592 A | 8/2000 | Vidal et al. |
| 6,173,717 B1 | 1/2001 | Schonert et al. |
| 6,241,971 B1 | 6/2001 | Fox et al. |
| 6,284,003 B1 | 9/2001 | Rose et al. |
| 6,309,426 B1 | 10/2001 | Dias et al. |
| 6,338,741 B1 | 1/2002 | Vidal et al. |
| 6,348,189 B1 | 2/2002 | Tanabe et al. |
| 6,348,200 B1 | 2/2002 | Nakajima et al. |
| 6,398,821 B1 | 6/2002 | Dias et al. |
| 6,458,906 B1 | 10/2002 | Torgerson et al. |
| 6,515,050 B1 | 2/2003 | Mitsuzuka et al. |
| 6,537,532 B1 | 3/2003 | Torgerson et al. |
| 6,569,412 B2 | 5/2003 | Yamaguchi et al. |
| 6,645,258 B2 | 11/2003 | Vidal et al. |
| 6,645,478 B2 | 11/2003 | Rollat et al. |
| 6,706,258 B1 | 3/2004 | Gallagher et al. |
| 6,730,789 B1 | 5/2004 | Birault et al. |
| 6,767,875 B1 | 7/2004 | Snyder et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,135,167 B2 | 11/2006 | Legrand et al. |
| 7,147,843 B2 | 12/2006 | Yoshida et al. |
| 7,151,079 B2 | 12/2006 | Fack et al. |
| 7,390,479 B2 | 6/2008 | Sockel et al. |
| 7,598,213 B2 | 10/2009 | Geary et al. |
| 7,612,141 B2 | 11/2009 | Sakai et al. |
| 7,815,901 B2 | 10/2010 | Mathonneau et al. |
| 7,905,926 B2 | 3/2011 | DeGeorge et al. |
| 7,972,388 B2 | 7/2011 | Hamilton et al. |
| 8,288,329 B2 | 10/2012 | Hata et al. |
| 8,298,519 B2 | 10/2012 | Adams et al. |
| 8,388,701 B2 | 3/2013 | Uellner et al. |
| 8,613,913 B2 | 12/2013 | Chang et al. |
| 8,642,021 B2 | 2/2014 | Brautigam et al. |
| 8,642,659 B2 | 2/2014 | Springer et al. |
| 9,095,518 B2 | 8/2015 | Pressly et al. |
| 9,144,537 B1 | 9/2015 | Pressly et al. |
| 9,175,114 B2 * | 11/2015 | Puerta .................. A61K 8/85 |
| 9,180,086 B2 * | 11/2015 | Cabourg ............... A61K 8/362 |
| 9,326,926 B2 | 5/2016 | Pressly et al. |
| 9,498,419 B2 | 11/2016 | Pressly et al. |
| 9,597,273 B2 | 3/2017 | Pressly et al. |
| 9,610,241 B2 | 4/2017 | Cabourg et al. |
| 9,918,923 B1 | 3/2018 | Naiberk et al. |
| 9,993,406 B2 | 6/2018 | Manneck et al. |
| 10,004,673 B1 | 6/2018 | Elsen-Wahrer et al. |
| 10,231,915 B2 | 3/2019 | Dreher et al. |
| 10,561,599 B2 | 2/2020 | Patterson et al. |
| 10,576,307 B2 | 3/2020 | Patterson et al. |
| 2001/0029637 A1 | 10/2001 | Nakashimada et al. |
| 2001/0042276 A1 | 11/2001 | Kawasoe et al. |
| 2001/0052354 A1 | 12/2001 | Nishibe et al. |
| 2002/0029429 A1 | 3/2002 | Dias et al. |
| 2002/0032933 A1 | 3/2002 | Dias et al. |
| 2002/0050013 A1 | 5/2002 | Vidal et al. |
| 2002/0053110 A1 | 5/2002 | Dias et al. |
| 2002/0155081 A1 | 10/2002 | Coope |
| 2002/0189034 A1 | 12/2002 | Kitabata et al. |
| 2003/0019051 A9 | 1/2003 | Vidal et al. |
| 2003/0049222 A1 | 3/2003 | Akhter et al. |
| 2003/0072962 A1 | 4/2003 | Matsuzaki et al. |
| 2003/0083380 A1 | 5/2003 | Yu et al. |
| 2003/0152543 A1 | 8/2003 | Legrand et al. |
| 2003/0215415 A1 | 11/2003 | Mitsumatsu et al. |
| 2004/0034944 A1 | 2/2004 | Legrand et al. |
| 2004/0034946 A1 | 2/2004 | Legrand et al. |
| 2004/0067212 A1 | 4/2004 | Tokuyama et al. |
| 2004/0086475 A1 | 5/2004 | Boswell et al. |
| 2004/0088800 A1 | 5/2004 | Cotteret |
| 2004/0156877 A1 | 8/2004 | Tokuyama et al. |
| 2004/0181883 A1 | 9/2004 | Legrand et al. |
| 2004/0202689 A1 | 10/2004 | Subramanyan et al. |
| 2004/0216244 A1 | 11/2004 | Cotteret et al. |
| 2004/0228580 A1 | 11/2004 | Lee et al. |
| 2004/0241114 A1 | 12/2004 | Gupta |
| 2004/0256598 A1 | 12/2004 | Plos et al. |
| 2004/0258652 A1 | 12/2004 | Pascaly et al. |
| 2005/0036970 A1 | 2/2005 | Sabbagh et al. |

(56) References Cited

U.S. PATENT DOCUMENTS

| | | |
|---|---|---|
| 2005/0087718 A1 | 4/2005 | Okada |
| 2005/0176615 A1 | 8/2005 | Kinoshita et al. |
| 2005/0191263 A1 | 9/2005 | Ueyama et al. |
| 2005/0193501 A1 | 9/2005 | Chan et al. |
| 2005/0201966 A1 | 9/2005 | Ueyama et al. |
| 2006/0024257 A1 | 2/2006 | Chang et al. |
| 2006/0075580 A1 | 4/2006 | Chan et al. |
| 2006/0093571 A1 | 5/2006 | Glinski |
| 2006/0166845 A1 | 7/2006 | Terada |
| 2006/0198807 A1 | 9/2006 | Morioka |
| 2006/0228316 A1 | 10/2006 | Cannell et al. |
| 2006/0251673 A1 | 11/2006 | Hwang et al. |
| 2007/0041921 A1 | 2/2007 | Neill et al. |
| 2007/0067924 A1 | 3/2007 | Beck et al. |
| 2007/0107142 A1 | 5/2007 | Nguyen et al. |
| 2007/0116661 A1 | 5/2007 | Mata |
| 2007/0160560 A1 | 7/2007 | Laurent et al. |
| 2007/0161543 A1 | 7/2007 | Yu et al. |
| 2007/0190008 A1 | 8/2007 | Campain et al. |
| 2007/0261594 A1 | 11/2007 | Vaskelis et al. |
| 2007/0264208 A1 | 11/2007 | Mougin et al. |
| 2008/0025937 A1 | 1/2008 | Cassier |
| 2008/0066773 A1 | 3/2008 | Anderson et al. |
| 2008/0138309 A1 | 6/2008 | Malle et al. |
| 2008/0141468 A1 | 6/2008 | Cotteret |
| 2008/0187506 A1 | 8/2008 | Carballada et al. |
| 2008/0226576 A1 | 9/2008 | Benabdillah et al. |
| 2008/0233072 A1 | 9/2008 | Bureiko et al. |
| 2008/0306025 A1 | 12/2008 | Yu et al. |
| 2009/0022681 A1 | 1/2009 | Carballada et al. |
| 2009/0053165 A1 | 2/2009 | Brown et al. |
| 2009/0126756 A1 | 5/2009 | Syed et al. |
| 2009/0208499 A1 | 8/2009 | Yu et al. |
| 2009/0214628 A1 | 8/2009 | de Rijk |
| 2009/0252697 A1 | 10/2009 | Barbarat et al. |
| 2009/0274677 A1 | 11/2009 | Isaacs et al. |
| 2010/0004391 A1 | 1/2010 | Haddleton et al. |
| 2010/0015079 A1 | 1/2010 | Schraderq |
| 2010/0081716 A1 | 4/2010 | Matsunaga et al. |
| 2010/0119468 A1 | 5/2010 | Garcia Castro et al. |
| 2010/0154140 A1 | 6/2010 | Simonet et al. |
| 2010/0158845 A1 | 6/2010 | Ellington et al. |
| 2010/0158964 A1 | 6/2010 | Cunningham et al. |
| 2010/0189795 A1 | 7/2010 | Dreher |
| 2010/0202998 A1 | 8/2010 | Ramos-Stanbury et al. |
| 2010/0247463 A1 | 9/2010 | Yu et al. |
| 2010/0303748 A1 | 12/2010 | Hercouet |
| 2011/0056508 A1 | 3/2011 | Gross et al. |
| 2011/0061671 A1 | 3/2011 | Neplaz et al. |
| 2011/0150804 A1 | 6/2011 | Nojiri et al. |
| 2011/0213033 A1 | 9/2011 | Tokuyama et al. |
| 2011/0256084 A1 | 10/2011 | Dixon et al. |
| 2011/0311463 A1 | 12/2011 | Diamond et al. |
| 2012/0015894 A1 | 1/2012 | Terada |
| 2012/0022037 A1 | 1/2012 | Terada |
| 2012/0064137 A1 | 3/2012 | Kawai |
| 2012/0114583 A1 | 5/2012 | Giesen et al. |
| 2012/0118316 A1 | 5/2012 | Uellner et al. |
| 2012/0180807 A1 | 7/2012 | Flohr |
| 2012/0244082 A1 | 9/2012 | Sulzbach et al. |
| 2012/0288459 A1 | 11/2012 | Burg et al. |
| 2012/0329650 A1 | 12/2012 | Lopez-Cervantes |
| 2013/0016246 A1 | 1/2013 | Hatanaka et al. |
| 2013/0034515 A1 | 2/2013 | Stone et al. |
| 2013/0102513 A1 | 4/2013 | Terada |
| 2013/0118996 A1 | 5/2013 | Kaplan |
| 2013/0149274 A1 | 6/2013 | Nguyen et al. |
| 2013/0152959 A1 | 6/2013 | Genain et al. |
| 2013/0156716 A1 | 6/2013 | Yontz |
| 2013/0164240 A1 | 6/2013 | Schrott |
| 2013/0172518 A1 | 7/2013 | Huang et al. |
| 2013/0216491 A1 | 8/2013 | Ogihara et al. |
| 2013/0233331 A1 | 9/2013 | Khenniche et al. |
| 2013/0233332 A1 | 9/2013 | Khenniche et al. |
| 2013/0251656 A1 | 9/2013 | Khenniche et al. |
| 2013/0266529 A1 | 10/2013 | Deconinck et al. |
| 2013/0309190 A1 | 11/2013 | Dimotakis et al. |
| 2014/0171354 A1 | 6/2014 | Miralles et al. |
| 2014/0186283 A1 | 7/2014 | Cabourg et al. |
| 2014/0196741 A1 | 7/2014 | Cabourg et al. |
| 2014/0246041 A1 | 9/2014 | Krueger |
| 2015/0004117 A1 | 1/2015 | Tan et al. |
| 2015/0004119 A1 | 1/2015 | Tan et al. |
| 2015/0034117 A1 | 2/2015 | Pressly et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0053228 A1 | 2/2015 | Bonauer et al. |
| 2015/0053230 A1 | 2/2015 | Myatt |
| 2015/0090285 A1 | 4/2015 | Worner et al. |
| 2015/0157544 A1 | 6/2015 | Briggs et al. |
| 2015/0252302 A1* | 9/2015 | Rieth ............... C11D 3/2072 514/772 |
| 2015/0283041 A1 | 10/2015 | Benn et al. |
| 2015/0290101 A1 | 10/2015 | Pressly et al. |
| 2015/0297496 A1 | 10/2015 | Kroon et al. |
| 2015/0313816 A1 | 11/2015 | Daubresse |
| 2015/0328102 A1 | 11/2015 | Pressly et al. |
| 2016/0058688 A1 | 3/2016 | Anderheggen et al. |
| 2016/0081899 A1 | 3/2016 | Pressly et al. |
| 2016/0175238 A1 | 6/2016 | Shin et al. |
| 2016/0193129 A1 | 7/2016 | Pressly et al. |
| 2016/0235649 A1 | 8/2016 | Streuli |
| 2016/0263003 A1 | 9/2016 | Pressly et al. |
| 2016/0310394 A1 | 10/2016 | Pressly et al. |
| 2016/0331664 A1 | 11/2016 | Anderheggen et al. |
| 2016/0348037 A1 | 12/2016 | Findlay et al. |
| 2017/0007518 A1 | 1/2017 | Everaert et al. |
| 2017/0112740 A1 | 4/2017 | Schoepgens et al. |
| 2017/0112743 A1 | 4/2017 | Schoepgens et al. |
| 2017/0113071 A1 | 4/2017 | Schoepgens et al. |
| 2017/0119122 A1 | 5/2017 | Rautenberg-Groth et al. |
| 2017/0128334 A1 | 5/2017 | Schoepgens et al. |
| 2017/0128342 A1 | 5/2017 | Schoepgens et al. |
| 2017/0143611 A1 | 5/2017 | Hippe et al. |
| 2017/0151143 A1 | 6/2017 | Scheunemann et al. |
| 2017/0151144 A1 | 6/2017 | Scheunemann et al. |
| 2017/0151146 A1 | 6/2017 | Scheunemann et al. |
| 2017/0151147 A1 | 6/2017 | Scheunemann et al. |
| 2017/0151156 A1 | 6/2017 | Scheunemann et al. |
| 2017/0157011 A1 | 6/2017 | Punyani et al. |
| 2017/0165161 A1 | 6/2017 | Manneck et al. |
| 2017/0246094 A1 | 8/2017 | Dreher et al. |
| 2017/0360658 A1 | 12/2017 | Ferrari et al. |
| 2018/0042830 A1 | 2/2018 | Dreher et al. |
| 2018/0055751 A1 | 3/2018 | Gevgilili et al. |
| 2018/0116942 A1 | 5/2018 | Mahadeshwar et al. |
| 2018/0140531 A1 | 5/2018 | Singer et al. |
| 2018/0140532 A1 | 5/2018 | Singer et al. |
| 2018/0280267 A1 | 10/2018 | Rughani et al. |
| 2018/0280269 A1 | 10/2018 | Rughani et al. |
| 2018/0280270 A1 | 10/2018 | Rughani et al. |
| 2018/0280271 A1 | 10/2018 | Fack et al. |
| 2018/0338895 A1 | 11/2018 | Patterson et al. |
| 2019/0201309 A1 | 7/2019 | Machover et al. |
| 2020/0129405 A1 | 4/2020 | Mitchell et al. |

FOREIGN PATENT DOCUMENTS

| | | |
|---|---|---|
| DE | 3843892 A1 | 6/1990 |
| DE | 4133957 A1 | 4/1993 |
| DE | 4300320 A1 | 7/1994 |
| DE | 19543988 A1 | 5/1997 |
| DE | 29722990 U1 | 5/1999 |
| DE | 10051773 A1 | 4/2002 |
| DE | 10051774 A1 | 4/2002 |
| DE | 20208254 U1 | 8/2002 |
| DE | 102004052480 A1 | 5/2006 |
| DE | 202015104742 U1 | 10/2015 |
| DE | 102014213317 A1 | 1/2016 |
| DE | 102015223828 A1 | 9/2016 |
| DE | 10 2015 221460 A1 | 5/2017 |
| DE | 20 2017 001430 U1 | 7/2017 |
| DE | 102016200688 A1 | 7/2017 |

(56) References Cited

FOREIGN PATENT DOCUMENTS

| | | |
|---|---|---|
| EP | 0122324 A1 | 10/1984 |
| EP | 0159628 A2 | 10/1985 |
| EP | 0286261 A2 | 10/1988 |
| EP | 0298684 A1 | 1/1989 |
| EP | 0299764 A2 | 1/1989 |
| EP | 0512879 A2 | 11/1992 |
| EP | 0636358 A1 | 2/1995 |
| EP | 0714954 A2 | 6/1996 |
| EP | 0770375 A1 | 5/1997 |
| EP | 0855178 A2 | 7/1998 |
| EP | 0978272 A1 | 2/2000 |
| EP | 1118319 A1 | 7/2001 |
| EP | 1174112 A2 | 1/2002 |
| EP | 1541117 A1 | 6/2005 |
| EP | 1570832 A1 | 9/2005 |
| EP | 1779896 A2 | 5/2007 |
| EP | 1810657 A1 | 7/2007 |
| EP | 2123250 A1 | 11/2009 |
| EP | 2229933 A1 | 9/2010 |
| EP | 2295029 A1 | 3/2011 |
| EP | 2460511 A1 | 6/2012 |
| EP | 2471504 A1 | 7/2012 |
| EP | 2478892 A1 | 7/2012 |
| FR | 1492597 A | 8/1967 |
| FR | 1583363 A | 10/1969 |
| FR | 2162025 A | 7/1973 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2413907 A1 | 8/1979 |
| FR | 2505348 A1 | 11/1982 |
| FR | 2542997 A1 | 9/1984 |
| FR | 2733749 A1 | 11/1996 |
| FR | 2801308 A1 | 5/2001 |
| FR | 2886136 A1 | 12/2006 |
| FR | 2944441 A1 | 10/2010 |
| FR | 2966352 A1 | 4/2012 |
| FR | 2975899 A1 | 12/2012 |
| FR | 2975900 A1 | 12/2012 |
| GB | 713675 A | 8/1954 |
| GB | 741307 A | 11/1955 |
| GB | 773559 A | 4/1957 |
| GB | 1026978 A | 4/1966 |
| GB | 1125794 A | 8/1968 |
| GB | 1153196 A | 5/1969 |
| GB | 1260451 A | 1/1972 |
| GB | 1546809 A | 5/1979 |
| GB | 1584364 A | 2/1981 |
| JP | 63-154611 A | 6/1988 |
| JP | 02-019576 A | 1/1990 |
| JP | H02-138110 A | 5/1990 |
| JP | 05-163124 A | 6/1993 |
| JP | H07-069847 A | 3/1995 |
| JP | 08-198732 A | 8/1996 |
| JP | H08-509478 A | 10/1996 |
| JP | 2002-356408 A | 12/2002 |
| JP | 2005-154348 A | 6/2005 |
| JP | 2006-327994 A | 12/2006 |
| JP | 2009-007283 A | 1/2009 |
| JP | 2010-155823 A | 7/2010 |
| JP | 2012-515218 A | 7/2012 |
| JP | 2015-086211 A | 5/2015 |
| JP | 2016-003185 A | 1/2016 |
| JP | 2017-095451 A | 6/2017 |
| JP | 2018-514570 A | 6/2018 |
| KR | 10-2001-0039848 A | 7/2001 |
| KR | 2003-0003970 A | 1/2003 |
| KR | 10-2004-0098688 A | 11/2004 |
| KR | 10-2006-0059564 A | 6/2006 |
| KR | 10-2016-0064420 A | 6/2016 |
| RU | 2229281 C1 | 5/2004 |
| WO | 93/00882 A1 | 1/1993 |
| WO | 93/08787 A2 | 5/1993 |
| WO | 94/08969 A1 | 4/1994 |
| WO | 94/08970 A1 | 4/1994 |
| WO | 95/01152 A1 | 1/1995 |
| WO | 95/01772 A1 | 1/1995 |
| WO | 95/15144 A1 | 6/1995 |
| WO | 96/15765 A1 | 5/1996 |
| WO | 97/24106 A1 | 7/1997 |
| WO | 98/56333 A1 | 12/1998 |
| WO | 99/11226 A1 | 3/1999 |
| WO | 99/66793 A1 | 12/1999 |
| WO | 01/35912 A1 | 5/2001 |
| WO | 01/47486 A1 | 7/2001 |
| WO | 01/52005 A1 | 7/2001 |
| WO | 02/32383 A2 | 4/2002 |
| WO | 02/32386 A2 | 4/2002 |
| WO | 02/055034 A2 | 7/2002 |
| WO | 2004/019858 A2 | 3/2004 |
| WO | 2005/058258 A1 | 6/2005 |
| WO | 2006/011771 A1 | 2/2006 |
| WO | 2006/134051 A1 | 12/2006 |
| WO | 2007/003307 A1 | 1/2007 |
| WO | 2007/038733 A1 | 4/2007 |
| WO | 2009/024936 A2 | 2/2009 |
| WO | 2010/049434 A2 | 5/2010 |
| WO | 2011/134785 A2 | 11/2011 |
| WO | 2012/080321 A2 | 6/2012 |
| WO | 2012/084532 A2 | 6/2012 |
| WO | 2012/164064 A1 | 12/2012 |
| WO | 2013/136480 A1 | 9/2013 |
| WO | 2014/016407 A1 | 1/2014 |
| WO | 2014/072490 A1 | 5/2014 |
| WO | 2014/118212 A1 | 8/2014 |
| WO | 2014/125452 A1 | 8/2014 |
| WO | 2014/167508 A1 | 10/2014 |
| WO | 2014/207097 A1 | 12/2014 |
| WO | 2015/017768 A1 | 2/2015 |
| WO | 2015/026994 A1 | 2/2015 |
| WO | 2015/058942 A1 | 4/2015 |
| WO | 2015/069823 A1 | 5/2015 |
| WO | 2015/075064 A2 | 5/2015 |
| WO | 2015/118357 A2 | 8/2015 |
| WO | 2015/175986 A1 | 11/2015 |
| WO | 2016/005114 A1 | 1/2016 |
| WO | 2016/005144 A1 | 1/2016 |
| WO | 2016/069877 A1 | 5/2016 |
| WO | 2016/091492 A1 | 6/2016 |
| WO | 2016/100885 A1 | 6/2016 |
| WO | 2016/102543 A1 | 6/2016 |
| WO | 2016/120642 A1 | 8/2016 |
| WO | 2016/161360 A1 | 10/2016 |
| WO | 2016/179017 A1 | 11/2016 |
| WO | 2016/198203 A1 | 12/2016 |
| WO | 2017/041903 A1 | 3/2017 |
| WO | 2017/041905 A1 | 3/2017 |
| WO | 2017/041906 A1 | 3/2017 |
| WO | 2017/041907 A1 | 3/2017 |
| WO | 2017/041908 A1 | 3/2017 |
| WO | 2017/041909 A1 | 3/2017 |
| WO | 2017/041910 A1 | 3/2017 |
| WO | 2017/059646 A1 | 4/2017 |
| WO | 2017/085117 A1 | 5/2017 |
| WO | 2017/091794 A1 | 6/2017 |
| WO | 2017/091796 A1 | 6/2017 |
| WO | 2017/091797 A1 | 6/2017 |
| WO | 2017/091800 A1 | 6/2017 |
| WO | 2017/102855 A1 | 6/2017 |
| WO | 2017/102936 A1 | 6/2017 |
| WO | 2017/207198 A1 | 12/2017 |
| WO | 2018/081399 A1 | 5/2018 |
| WO | 2018/085478 A1 | 5/2018 |

OTHER PUBLICATIONS

Mintel: "Conditioner," Unilever, XP055576888, Database accession No. 1419415, Oct. 21, 2010.

(56) References Cited

OTHER PUBLICATIONS

Mintel: "Conditioner," Unilever, XP055576893, Database accession No. 3014885, Mar. 2, 2015.
"Olaplex Alleges Patent Infringement by L'OREAL re Hairbond-Building Prior to Colouring," Focus on Pigments, vol. 2017, No. 3, Mar. 31, 2017, p. 7.
International Preliminary Report on Patentability for counterpart Application No. PCT/US2017/058495, dated May 9, 2019.
Notice of Allowance for co-pending U.S. Appl. No. 15/778,803, dated Jun. 3, 2019.
EP Office Action for counterpart Application No. 16789846, dated Jan. 23, 2019.
Written Opinion for counterpart EP Application No. 16789846, dated Jan. 23, 2019.
International Preliminary Report on Patentability for counterpart Application No. PCT/US2016/063724, dated Jun. 7, 2018.
Brazilian Office Action for counterpart Application No. BR112018010381-0, dated Nov. 25, 2019.
Brazilian Office Action for counterpart Application No. BR112018010357-8, dated Nov. 25, 2019.
Mexican Office Action for counterpart Application No. MX/a/2018/005829, dated [unknown].
Brazilian Office Action for counterpart Application No. BR112018010344, dated Nov. 25, 2019.
Mexican Office Action for counterpart Application No. MX/a/2017/013983, dated Dec. 16, 2019 (partial translation).
Translated Japanese Office Action for counterpart Application No. 2018-526844, dated Dec. 23, 2019.
Translated Japanese Office Action for counterpart Application No. 2018-526845, dated Dec. 23, 2019.
Translated Japanese Office Action for counterpart Application No. 2018-546409, dated Dec. 23, 2019.
International Preliminary Report on Patentability for counterpart Application No. PCT/US2016/063727, dated Jun. 7, 2018.
International Preliminary Report on Patentability for counterpart Application No. PCT/US2016/063732, dated Jun. 7, 2018.
International Preliminary Report on Patentability for counterpart Application No. PCT/US2016/063728, dated Jun. 7, 2018.
International Search Report for counterpart Application No. PCT/US2016/063727, dated Feb. 8, 2017.
International Search Report for counterpart Application No. PCT/US2016/063732, dated Feb. 6, 2017.
International Search Report for counterpart Application No. PCT/US2016/063728, dated Feb. 1, 2017.
International Search Report and Written Opinion for counterpart Application No. PCT/US2016/030172, dated Sep. 19, 2016.
International Search Report and Written Opinion for counterpart Application No. PCT/US2016/063724, dated Feb. 2, 2017.
Mintel: "Abundant Volume Conditioner," Alterna Professional Haircare, Database Record No. 2177147, Sep. 2013.
Mintel: "Hair Colourant," Catzy Hair Colourant, Database Record ID 743114, Jul. 2007, 4 pages.
Mintel: "Combing Cream," Devintex Cosmeticos, Database Record No. 1595490, Jul. 2011.
Mintel: "Combing Cream," Devintex Cosmeticos, Database Record No. 1595658, Jul. 2011.
Mintel: "Conditioner," Devintex Cosmeticos, Database Record No. 1595545, Jul. 2011.
Mintel: "Conditioner," Laperie Haircare, Database Record No. 3645337, Feb. 2016.
Mintel: "Conditioner," Laperie Haircare, Database Record No. 3790215, Feb. 2016.
Mintel: "Conditioner," Liqwd, Database Record No. 1172691, Sep. 2009.
Mintel: "Conditioner," TIGI, Database Record No. 1442418, Nov. 2010.
Mintel: "Conditioner," TIGI International, Database Record No. 1445427, Nov. 2010.
Mintel: "Conditioner," TGI International, Database Record No. 3280151, Jul. 2015.
Mintel, "Masque for Beautiful Color," Oribe Hair Care, Database Record No. 1522953, Mar. 2011.
Mintel: "Moisturizing Conditioner," Frederic Fekkai, Datablase Record No. 1507159, Mar. 2011.
Mintel: "Post-Service Perfector," Redken, Database Record No. 4326453, Nov. 2016.
Mintel: "Step 3-Conditioner," L'OREAL, Database Record No. 4353779, Oct. 2016.
International Preliminary Report on Patentability for counterpart Application No. PCT/US2016/30172, dated Jun. 19, 2017.
Petition for Post-Grant Review of U.S. Pat. No. 9,498,419, filed Jan. 31, 2017, with Exhibits.
Non-Final Office Action for copending U.S. Appl. No. 15/484,625, dated Jun. 21, 2017.
Final Office Action for copending U.S. Appl. No. 15/484,625, dated Nov. 14, 2017.
Non-Final Office Action for copending U.S. Appl. No. 15/484,663, dated Jun. 21, 2017.
Final Office Action for copending U.S. Appl. No. 15/484,663, dated Nov. 28, 2017.
Non-Final Office Action for copending U.S. Appl. No. 15/339,035, dated Jan. 10, 2018.
International Search Report for counterpart Application No. PCT/US2017/058495, dated Jan. 5, 2018.
Third Party Submission for U.S. Appl. No. 15/484,663, filed Feb. 28, 2018, with attachments.
Pressly, Eric et al., U.S. Appl. No. 61/994,709, filed May 16, 2014 and became publicly available on Nov. 19, 2015.
Estetica: the hairstyling professional magazine, (http://estetica.it/int/a/schwarzkopf-professional-launches-fibreplex), "Schwarzkopf Professional Launches Fibreplex®," published Sep. 23, 2015 reporting that Fibreplex was launched during Sep. 2015.
Declaration Under 37 C.F.R. 1.132 of Eric D. Pressly, Ph.D. submitted Aug. 23, 2016, Exhibit 1009.
Response to Office Action dated Aug. 23, 2016, Exhibit No. 1010.
Notice of Allowance for U.S. Appl. No. 15/087,415, dated Sep. 26, 2016, Exhibit 1011.
Clausen et al., "Hair Preparations," Ullman's Encyclopedia of Industrial Chemistry, (Jul. 15, 2006), http://onlinelibrary.wiley.com/doi/10.1002/14356007.a12_571.pub2, Exhibit 1012.
Declaration Under 37 C.F.R. 1.132 of Eric D. Pressly, Ph.D. submitted Sep. 14, 2016, Exhibit 1013.
Office Action for U.S. Appl. No. 15/087,415, dated May 23, 2016, Exhibit 1014.
John Corbett, Hair Colorants: Chemistry and Toxicology 1-54 (1998), Exhibit 1015.
Webster's Third International New Dictionary 40 (3d. ed. 2002), Exhibit 1017.
Notice of Third Party Submission for copending U.S. Appl. No. 15/484,663, mailed Mar. 5, 2018.
Notice of Allowance for copending U.S. Appl. No. 15/484,663, dated Jun. 18, 2018.
Non-Final Office Action for copending U.S. Appl. No. 15/484,625, dated Jun. 20, 2018.
Brazilian Written Opinion for counterpart Application No. BR112018010341, dated Nov. 25, 2019.
Non-Final Office Action for counterpart Japanese Application No. 2018-546408, dated Jan. 6, 2020.
Mintel: "Tonic," Dr. Kurt Wolff, Dr. Wolff Plantur 39, ID#3133037, Apr. 2015.
Mintel: "Conditioner," LG Household & Health Care, Beyond Professional, ID#3240637, Jun. 2015.
Bayraktar, V.N., "Organic Acids Concentration in Wine Stocks After *Saccharomyces cereviisilae* Fermentation," Biotechnologia Acta, vol. 6, No. 2, Jan. 1, 2013, pp. 97-106.
Supplementary European Search Report for counterpart Application EP16789846, dated Oct. 30, 2018.
Extended European Search Report for counterpart Application No. 16869327.3-1114, dated Jun. 17, 2019.
Mintel: "Detox 7 Day Cure Purifying Serum," XP055593471, Jeanne Gatineau, Feb. 11, 2013.
Extended European Search Report for counterpart Application No. 16869326.5-1114, dated Jun. 26, 2019.

(56) References Cited

OTHER PUBLICATIONS

Extended European Search Report for counterpart Application No. 16869330.7-1114, dated Jul. 5, 2019.
Translation of Mexican Office Action for counterpart Application No. MX/a/2018/005829, dated Jun. 13, 2019.
Brazilian Office Action for counterpart Application No. BR112017023380-0, dated Oct. 10, 2019, with translation.
Non-Final Office Action for co-pending U.S. Appl. No. 15/339,035, dated Aug. 20, 2019.
Mexican Office Action for counterpart Application No. MX/a/2017/013983, dated Jul. 2, 2019.
Notice of Allowance for co-pending U.S. Appl. No. 16/042,478, dated Sep. 25, 2019.
Non-Final Office Action for co-pending U.S. Appl. No. 15/778,807, dated Sep. 30, 2019.
Final Office Action for copending U.S. Appl. No. 15/778,807, dated Mar. 13, 2020.
Final Office Action for copending U.S. Appl. No. 15/339,035, dated Apr. 10, 2020.
Non-Final Office Action for copending U.S. Appl. No. 16/273,787, dated Apr. 9, 2020.
International Search Report and Written Opinion for counterpart Application No. PCTUS2017/059827, dated Jun. 28 2018.
"LAMESOFT® PO 65 Datasheet," Retrieved from the internet on Jun. 7, 2018, http://e-applications.basf-ag.de/data/basf-pcan/pds2/pds2-web.nsf.
Non-Final Office Action for copending U.S. Appl. No. 15/356,967, dated May 3, 2017.
Final Office Action for copending U.S. Appl. No. 15/356,967, dated Dec. 4, 2017.
Non-Final Office Action for copending U.S. Appl. No. 15/356,967, dated Aug. 24, 2018.
Final Office Action for copending U.S. Appl. No. 15/356,967, dated Apr. 11, 2019.
Non-Final Office Action for copending U.S. Appl. No. 15/356,967, dated Feb. 21, 2020.
International Search Report and Written Opinion for counterpart Application No. PCT/US2017/059817, dated Feb. 6, 2018.
Non-Final Office Action for copending U.S. Appl. No. 15/357,056, dated Apr. 16, 2020.
Non-Final Office Action for copending U.S. Appl. No. 15/942,042, dated Jan. 24, 2020.
ALS "Cocamidopropyl betaine," printed 2020; https://www.caslab.com/Cocamidopropyl_betaine_CAS_61789-40-0.
International Search Report and Written Opinion for counterpart Application No. PCT/US2018/025466, dated Jul. 9, 2018.
International Preliminary Report on Patentability for counterpart Application No. PCT/US2018/025466, dated Oct. 1, 2019.
International Search Report and Written Opinion for counterpart Application No. PCT/US2018/025448, dated Jul. 9, 2018.
International Preliminary Report on Patentability for counterpart Application No. PCT/US2018/025448, dated Oct. 1, 2019.
International Search Report and Written Opinion for counterpart Application No. PCT/US2018/025431, dated Jun. 20, 2018.
International Preliminary Report on Patentability for counterpart Application No. PCT/US2018/025431, dated Oct. 1, 2019.
International Search Report and Written Opinion for counterpart Application No. PCT/US2018/025418, dated Jun. 21, 2018.
International Preliminary Report on Patentability for counterpart Application No. PCT/US2018/025418, dated Oct. 1, 2019.
Notice of Allowance for copending U.S. Appl. No. 15/604,152, dated Oct. 2, 2019 (now U.S. Pat. No. 10,561,599).
Non-Final Office Action for copending U.S. Appl. No. 15/604,152, dated Jun. 13, 2019.
Olaplex with relaxers, OLAPLEX™, pp. 1-2, Apr. 11, 2017, https://olaplex.es/olaplex-with-relaxers/.
Relaxers, resource Library, Olaplex Education, pp. 1-2, Apr. 11, 2017, https://help.olaplex.com/detail/relaxers.
Notice of Allowability for copending U.S. Appl. No. 15/604,152, dated Dec. 10, 2019.
International Search Report and Written Opinion for counterpart Application No. PCT/US2018/034366, dated Jul. 25, 2018.
Anonymous: "Curly Hair Conditioner," Mintel, GNPD, XP002782449, 2015, pp. 1-2.
Corrected Notice of Allowability for copending U.S. Appl. No. 15/604,189, dated Dec. 11, 2019 (now U.S. Pat. No. 10,576,307).
Notice of Allowance for copending U.S. Appl. No. 15/604,189, dated Oct. 22, 2019.
Non-Final Office Action for copending U.S. Appl. No. 15/604,189, dated Apr. 8, 2019.
International Search Report and Written Opinion for counterpart Application No. PCT/US2018/034371, dated Nov. 16, 2018.
Mintel: "Hydrating Hair Colour," Garnier, Jan. 2017, pp. 1-6.
Mintel, "Masque Force Architecte Reconstructing Masque," L'Oreal, Feb. 2012, pp. 1-6.
Final Office Action for copending U.S. Appl. No. 15/603,889, dated Jul. 12, 2019.
Non-Final Office Action for copending U.S. Appl. No. 15/603,889, dated Jan. 2, 2019.
International Search Report and Written Opinion for counterpart Application No. PCT/US2018/034378, dated Jul. 24, 2018.
Mintel: "Step 3-Conditioner," L'OREAL, Database Record No. 4609117, Feb. 2017.
Final Office Action for copending U.S. Appl. No. 16/234,883, dated Mar. 11, 2020.
Non-Final Office Action for copending U.S. Appl. No. 16/234,883, dated Sep. 16, 2019.
International Search Report and Written Opinion for counterpart Application No. PCT/US2018/067814, dated Feb. 25, 2019.
Final Office Action for copending U.S. Appl. No. 16/176,350, dated Apr. 8, 2020.
Non-Final Office Action for copending U.S. Appl. No. 16/176,350, dated Nov. 14, 2019.
International Search Report and Written Opinion for counterpart Application No. PCT/US2019/059002, dated Feb. 4, 2020.
Korean Notification of Reason for Refusal for counterpart Application No. KR10-2017-7034789, dated May 19, 2020 (translation).
Final Office Action for copending U.S. Appl. No. 15/942,042, dated Jun. 1, 2020.
Japanese Notice of Reason for Refusal for counterpart Application No. 2017-557074, dated Jun. 1, 2020.
Russian Office Action for counterpart Application No. 2018114758/04, dated Dec. 13, 2019.
Translated Notification of Reason for Refusal for counterpart KR Application No. 10-2018-7017668, dated Jan. 21, 2020.
Translated Office Action for counterpart Russian Application No. 2017134681/04(0060925), dated Dec. 30, 2019.
Non-Final Office Action for copending U.S. Appl No. 15/942,085, dated Jun. 19, 2020.
Shiseido Super Mild Hair Care—Shampoo and Conditioner Refill Set. https://web.archive.org/web/20160326190615/http://www.truenu.com/TR/Shiseido-Super-Mild-Hair-Care-Shampoo-Conditioner-Refill-Set-Two-400ml-Refill-Pouches-Details.html. Published Mar. 26, 2016.
Non-Final Office Action for copending U.S. Appl. No. 15/941,916, dated Jun. 24, 2020.
Non-Final Office Action for copending U.S. Appl. No. 15/941,965, dated Jul. 15, 2020.
Third Party Observation for counterpart Application No. EP 20160869330, dated Jun. 26, 2020.
Third Party Observation for counterpart Application No. EP 20160869326, dated Jul. 2, 2020.
Third Party Observation for counterpart Application No. EP 20160869327, dated Jul. 2, 2020.
Translated Japanese Office Action for counterpart Application No. 2018-526844, dated Aug. 3, 2020.

\* cited by examiner

COMPOSITIONS FOR TREATING THE HAIR

CROSS REFERENCE TO RELATED APPLICATIONS

This is a national stage application of PCT/US2016/063732, filed internationally on Nov. 24, 2016, which claims priority to U.S. Provisional Application No. 62/259,578, filed Nov. 24, 2015, both of which are incorporated by reference herein in their entireties.

TECHNICAL FIELD

The present disclosure relates to compositions for use in treating keratinous substrates, such as the hair.

BACKGROUND

It is known that consumers desire to use cosmetic and care compositions that enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve chemical treatment of the hair.

The process of changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening, generally requires the use of compositions that comprise at least one oxidizing agent.

Lightening or lifting the color of the hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

In general, hair lightening or color lifting compositions and hair dyeing compositions possess an alkalinity such that these compositions have a pH value of above 7, typically being at pH 9 and above, and may generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effective alter the shape of the hair, these chemical treatments can damage the hair fibers and/or irritate the scalp. Thus, in order to reduce or avoid the drawbacks mentioned above, as well as to improve the cosmetic performance of the compositions, the use of new and additional components and novel combinations of ingredients are continuously sought.

However, the choice of components or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can treat the hair, e.g. lift the color of hair and/or deposit color onto hair in an efficient manner, while providing other cosmetic advantages such as shine, conditioning, fiber strength, and/or a healthy appearance to the hair, but avoiding or minimizing damage to the hair.

Further, both natural and sensitized or chemically treated hair can contain several kinds of negatively charged moieties, for example, carboxylates (resulting from the hydrolysis of amino acids and thioester bonds) and/or sulfonates (resulting from the oxidation of disulfide bonds). These negatively charged moieties can degrade the cosmetic properties of the hair.

Moreover, when hair is chemically treated or damaged, the disulfide bonds in hair (disulfide linkages between two cysteine units) can be reduced or broken, resulting in the formation of thiol groups and/or cysteic acid. Cysteine bridges, or disulfide bonds, are the strongest bonds present in the internal network of hair and play a key role in hair strength. Cosmetic treatments, such as bleaching, straightening, or permanent waving the hair, can permanently alter these bonds leading to the formation of cysteic acid. As such, increased amounts of cysteic acid in the hair suggest that the hair is damaged.

Thus, one objective of the disclosure is to provide novel compositions that can provide advantageous effects such as strengthening of the hair fiber, protecting hair fibers from damage or further damage, enhanced properties such as softness, shine, conditioning, healthy appearance, while at the same time, providing desired effects such as coloring, lightening, straightening, relaxing, and/or shaping.

SUMMARY

The present disclosure relates to compositions and systems for treating keratinous substrates, such as the hair, as well as methods for treating keratinous substrates with the compositions and systems disclosed herein.

According to various embodiments, the disclosure relates to hair treatment compositions comprising 2-(2-aminoethoxy)ethanol (2-2 AEE) and at least one carboxylic acid. The treatment compositions may optionally be used in conjunction with chemical treatments such as compositions or agents for altering the color or shape of the hair, including hair coloring or hair lightening compositions, or hair-shaping compositions for straightening, relaxing, and/or permanent waving the hair, or may be used with compositions for treating the hair that are not color- or shape-altering compositions. The treatment compositions may also optionally be applied directly to the hair, and/or may be mixed with water or other solvent or composition and applied to the hair.

The disclosure further relates to hair conditioning compositions comprising 2-(2-aminoethoxy)ethanol and at least one carboxylic acid. In further embodiments, the disclosure relates to hair treatment systems comprising the treatment compositions and conditioning compositions according to the disclosure, and use of the systems in conjunction with compositions for altering the color and/or shape of the hair.

Exemplary methods comprise applying the treatment composition according to the disclosure to the hair before, during, and/or after application of a color-altering composition to the hair. Further exemplary methods comprise applying a conditioning composition according to the disclosure to the hair after application of the treatment composition. Methods according to the disclosure may provide for cosmetic advantages such as shine, conditioning, fiber strength, and/or a healthy appearance to the colored hair, and/or avoiding or minimizing damage to the hair that may otherwise occur with processes for altering hair either by coloring, lightening or other chemical processes the color of the hair.

Further exemplary methods comprise applying the treatment composition according to the disclosure to the hair before, during, and/or after application of a hair shaping composition to the hair. Methods according to the disclosure may provide for cosmetic advantages such as shine, conditioning, fiber strength, and/or a healthy appearance to the shaped hair, and minimizing damage to the hair that may otherwise occur with processes for altering hair by shaping or other chemical processes.

Further exemplary methods comprise applying the treatment composition according to the disclosure to the hair before, during, and/or after application of a composition that is not a color- or shape-altering composition to the hair. Still further exemplary methods comprise applying the treatment composition according to the disclosure to the hair before, during, and/or after application of water or other solvent to the hair. Methods according to the disclosure may provide for cosmetic advantages such as shine, conditioning, fiber strength, and/or a healthy appearance to the shaped hair, and minimizing damage to the hair that may otherwise occur with processes for altering hair either by coloring, lightening or other chemical processes.

According to various embodiments, exemplary hair treatment systems comprise treatment compositions comprising 2-(2-aminoethoxy)ethanol and at least one carboxylic acid; conditioning compositions comprising 2-(2-aminoethoxy)ethanol and at least one carboxylic acid; and optionally a composition or agent for altering the color or shape of the hair. In some embodiments, the at least one carboxylic acid in the treatment composition and the conditioning composition of the systems are the same. In other embodiments, the at least one carboxylic acid in the treatment composition and the conditioning composition of the systems are different. Further embodiments of hair treatment systems comprise treatment compositions comprising 2-(2-aminoethoxy)ethanol and at least one carboxylic acid chosen from oxalic acid, malic acid, and combinations thereof; conditioning compositions comprising 2-(2-aminoethoxy)ethanol and at least one carboxylic acid; and optionally a composition or agent for altering the color or shape of the hair. Still further embodiments of hair treatment systems comprise treatment compositions comprising 2-(2-aminoethoxy)ethanol and at least one carboxylic acid chosen from oxalic acid, malic acid, and combinations thereof; conditioning compositions comprising 2-(2-aminoethoxy)ethanol and at least one carboxylic acid; and optionally a composition or agent for altering the color or shape of the hair.

According to various embodiments, kits for treating the hair may comprise: a first compartment containing a treatment composition comprising 2-(2-aminoethoxy)ethanol and at least one carboxylic acid; and a second compartment containing a conditioning composition comprising 2-(2-aminoethoxy)ethanol and at least one carboxylic acid.

In further embodiments, kits for treating the hair or for altering the color of hair may comprise: a first compartment containing a treatment composition comprising 2-(2-aminoethoxy)ethanol and at least one carboxylic acid, and optionally a composition or agent for altering the color of the hair; and a second compartment containing a conditioning composition comprising 2-(2-aminoethoxy)ethanol and at least one carboxylic acid. In yet further embodiments, kits for treating the hair or altering the color of hair may comprise: a first compartment containing a treatment composition comprising 2-(2-aminoethoxy)ethanol and at least one carboxylic acid; a second compartment containing a conditioning composition comprising 2-(2-aminoethoxy)ethanol and at least one carboxylic acid; and one or more additional compartments containing one or more agents or compositions for altering the color of the hair.

In further embodiments, kits for treating the hair or for altering the shape of hair may comprise: a first compartment containing a treatment composition comprising 2-(2-aminoethoxy)ethanol and at least one carboxylic acid, and optionally a composition or agent for altering the shape of the hair; and a second compartment containing a conditioning composition comprising 2-(2-aminoethoxy)ethanol and at least one carboxylic acid. In still further embodiments, kits for treating the hair or altering the shape of hair may comprise: a first compartment containing a treatment composition comprising 2-(2-aminoethoxy)ethanol and at least one carboxylic acid; and a second compartment containing a conditioning composition comprising 2-(2-aminoethoxy)ethanol and at least one carboxylic acid; and one or more additional compartments containing one or more agents or compositions for altering the shape of the hair.

In further embodiments, kits for treating the hair or for altering the color or shape of hair may comprise: a first compartment containing a treatment composition comprising 2-(2-aminoethoxy)ethanol and at least one carboxylic acid chosen from oxalic acid, malic acid, and combinations thereof, and optionally a composition or agent for altering the color or shape of the hair; and a second compartment containing a conditioning composition comprising 2-(2-aminoethoxy)ethanol and at least one carboxylic acid. In yet further embodiments, kits for treating the hair or altering the color or shape of hair may comprise: a first compartment containing a treatment composition comprising 2-(2-aminoethoxy)ethanol and at least one carboxylic acid chosen from oxalic acid, malic acid, and combinations thereof; a second compartment containing a conditioning composition comprising 2-(2-aminoethoxy)ethanol and at least one carboxylic acid; and one or more additional compartments containing one or more agents or compositions for altering the color or shape of the hair.

BRIEF DESCRIPTION OF THE DRAWINGS

The present disclosure and claims can be better understood from the following detailed description either alone or together with the accompanying drawings. The drawings are included to provide a further understanding, and are incorporated in and constitute a part of this specification. The drawings illustrate one or more exemplary embodiments of the present disclosure and together with the description serve to explain various principles and operation.

FIG. 1 shows the sensorial comparison for 2-2AEE and citric acid.

FIG. 2 shows the sensorial comparison for 2-2AEE and malonic acid.

FIG. 3 shows the sensorial comparison for 2-2AEE and malic acid.

FIG. 4 shows the sensorial comparison for 2-2AEE and maleic acid.

FIG. 5 shows the sensorial comparison for 2-2AEE and oxalic acid.

DETAILED DESCRIPTION

Figure 1:
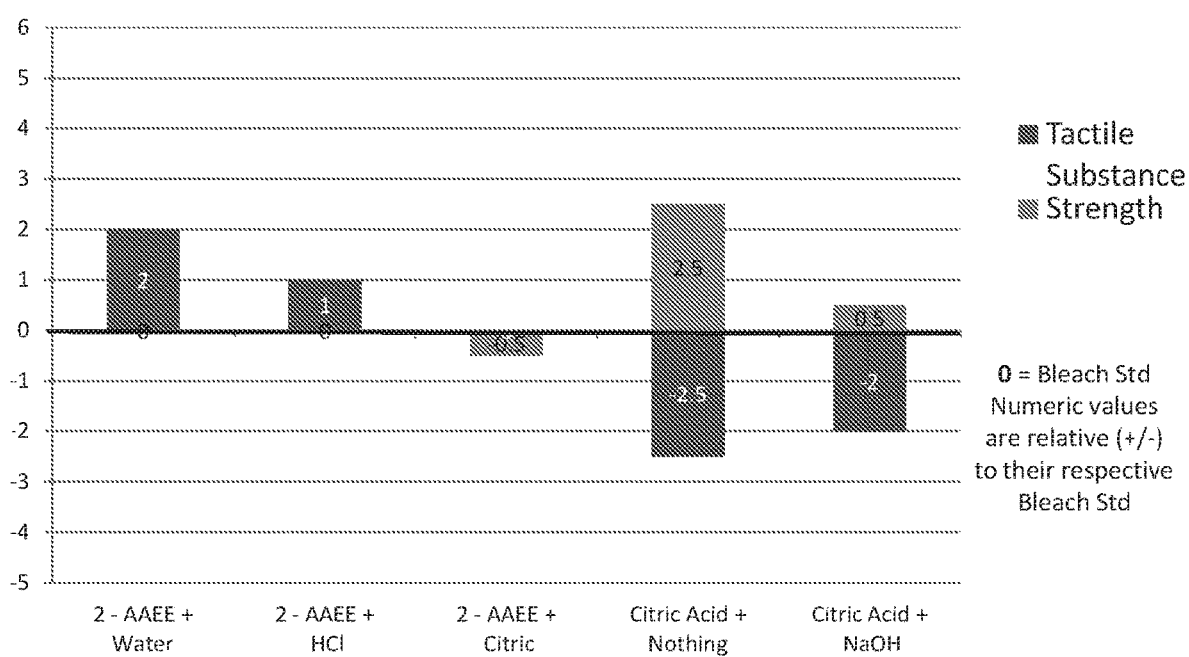
FIGS. 1-5 show sensorial data comparing strength and tactile substance for hair samples treated with a bleaching composition containing a hair treatment composition according to an embodiment of the disclosure containing 2-(2-aminoethoxy)ethanol (2-2AEE) and carboxylic acid relative to hair samples treated with 2-2AEE alone, 2-2AEE pH adjusted, carboxylic acid alone, and carboxylic acid pH adjusted, where the baseline (0) is a standard hair bleaching formulation with no additive.

Other than in the operating examples, or where otherwise indicated, all numbers expressing quantities of ingredients and/or reaction conditions are to be understood as being modified in all instances by the term "about" which can encompass ±10%, ±8%, ±6%, ±5%, ±4%, ±3%, ±2%, ±1%, or ±0.5%.

All numbers expressing pH values are to be understood as being modified in all instances by the term "about" which encompasses up to ±3%.

"At least one" as used herein means one or more and thus includes individual components as well as mixtures/combinations.

A "chemical treatment" composition as described herein may include any composition for chemically treating the hair, such as by way of non-limiting example, permanent waving, relaxing, straightening, oxidation dyeing, coloring, and lightening (e.g., bleaching, highlighting) the hair. The terms "chemical treatment composition," "color-altering composition," and "shape-altering composition," as well as variations thereof, may be used interchangeably herein without limitation.

"Systems" as used herein are meant to comprise treatment compositions according to the disclosure and conditioning compositions according to the disclosure.

The term "altering the color" or "color-altering" as used herein may refer to lifting or lightening the color of hair. It can also refer to dyeing or coloring hair or depositing color onto the hair. In certain instances, it refers to lifting or lightening the color of hair and depositing color onto the hair in one treatment.

The term "strength" as used herein may refer to the strength of the hair fiber with respect to the ease or difficulty of breaking a hair fiber, or to the amount of effort or force needed to break the fiber when the fiber is subjected to a pulling, tugging, stretching, combing, or brushing action.

The term "protecting" as used herein may refer to the prevention, minimization, or reduction of damage or further damage to hair.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

"(Meth)acrylic" as used herein, is understood to mean, within the meaning of the present patent application, "acrylic or methacrylic".

The term "neutralized" as used herein is intended to mean that the 2-(2-aminoethoxy)ethanol is protonated with a $H^+$ (proton) coming from the carboxylic acid(s).

The term "substantially free of (a component)" as defined herein means that the system or composition contains no appreciable amount of the component, for example, no more than about 1% by weight, no more than about 0.5% by weight, or no more than about 0.3% by weight, such as no more than about 0.1% by weight, based on the weight of the composition.

The term "free" or "completely free of (a component)" as defined herein means that the composition does not contain the component in any measurable degree by standard means.

As used herein, a carboxylic acid is described as being present in a composition regardless of whether the carboxylic acid is present in acid form or whether the acid is dissociated or forms a salt thereof, e.g. upon mixing with a solution or other formulation. Accordingly, if a composition (e.g. a treatment composition, a conditioning composition, or a composition for altering the color or shape of the hair) is described herein as comprising an acid, or comprising a certain amount of an acid, but the acid is dissociated or forms a salt in the composition, the description is intended to refer to the acid or amount thereof present before the dissociation or salt formation. By way of example only, if a treatment composition comprising 2-(2-aminoethoxy)ethanol and malic acid is mixed with a liquid hair bleaching composition, and in the hair bleaching composition the malic acid forms a salt of malic acid so that no or substantially no malic acid is present in the mixture, any reference to the hair bleaching composition comprising malic acid or a particular amount of malic acid is intended to refer to the malic acid or amount thereof present in the treatment composition before it is mixed with the hair bleaching composition.

Treatment Compositions

As described herein, the disclosure relates to treatment compositions comprising 2-(2-aminoethoxy)ethanol (2-2AEE) and at least one carboxylic acid. The treatment compositions can further comprise additional components, such as solvents. In various embodiments, the treatment composition consists essentially of 2-2AEE, one or more carboxylic acids, and one or more solvents. In other embodiments, the treatment composition consists essentially of 2-2AEE, one or more carboxylic acids, one or more solvents, and one or more coloring agents. In a further embodiment, the treatment composition consists of 2-2AEE, one or more carboxylic acids, and one or more solvents. In a further embodiment, the treatment composition consists of 2-2AEE, one or more carboxylic acids, one or more solvents, and one or more coloring agents.

2-(2-aminoethoxy)ethanol

The 2-(2-aminoethoxy)ethanol (2-2AEE) may be present in the treatment composition in an amount up to about 20%, such as up to about 19%, up to about 18%, up to about 17%, up to about 16%, up to about 15%, up to about 14%, up to about 13%, up to about 12%, up to about 11%, up to about 10%, up to about 9%, up to about 8%, up to about 7%, up to about 6%, up to about 5%, up to about 4%, up to about 3%, up to about 2%, up to about 1%, up to about 0.5%, or up to about 0.1% by weight, based on the weight of the treatment composition. By way of non-limiting example only, the 2-2AEE may be present in an amount ranging from about 0.0001% to about 20%, such as about 0.001% to about 15%, about 5 wt % to about 15 wt % 2-2AEE, such as from about 6 wt % to about 13 wt %, from about 7 wt % to about 12 wt %, from about 8 wt % to about 11 wt %, or from about 9 wt % to about 10 wt % 2-2AEE, based on the weight of the treatment composition.

Carboxylic Acids

The treatment compositions according to the disclosure may comprise at least one carboxylic acid. According to the disclosure, useful carboxylic acid include organic compounds that include, for example, one, two, three, or more carboxylic acid functional groups (COOH) and at least one carbon atom.

In certain exemplary, and non-limiting embodiments, the at least one carboxylic acid may be chosen from saturated or unsaturated, substituted or unsubstituted dicarboxylic acids, salts thereof, and mixtures thereof. By way of non-limiting example, the at least one carboxylic acid may be chosen from dicarboxylic acids of the following formula:

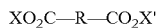

XO$_2$C—R—CO$_2$X' wherein:
—R is a cyclic or acyclic, saturated or unsaturated, linear or branched, C$_1$-C$_{100}$ hydrocarbon moiety comprising from 0 to 30 double and/or triple bonds and/or from 0 to 10 rings, and optionally interrupted by 1 to 30 heteroatoms chosen from O, N and S, and optionally substituted with 1 to 30 substituents chosen from a hydrogen atom, a hydroxyl (—OH) moiety, an amino (—NH$_2$) moiety, a (C$_1$-C$_{30}$)alkylamino moiety, a poly (C$_1$-C$_{30}$)alkylamino moiety, a hydroxy(C$_1$-C$_{30}$)alkylamino moiety, a polyhydroxy(C$_1$-C$_{30}$)alkylamino moiety, a C$_6$-C$_{30}$ aryl moiety, and in some embodiments —R may be omitted,
—X and X', independently denote a hydrogen atom, an ammonium ion, a ion of an alkali metal such as Li, Na, K, or an alkaline earth metal such as Be, Mg, Ca or an ion derived from an organic amine such as an alkylamine.

It is understood that the expression cyclic hydrocarbon moiety for the purposes of the present application is understood to mean a hydrocarbon moiety consisting of one or more rings or comprising one or more rings which are pendent or in the principle chain, it being possible for the rings to be saturated or unsaturated and to be substituted with one or more C$_1$-C$_{30}$ alkyl or alkenyl or hydroxyl or amino moieties.

By way of non-limiting example only, useful carboxylic acids may include oxalic acid, malonic acid, malic acid, glutaric acid, citraconic acid, citric acid, maleic acid, glycolic acid, succinic acid, adipic acid, tartaric acid, fumaric acid, sebacic acid, benzoic acid, and glyoxylic acid monohydrate, as well as combinations thereof. In at least one embodiment, the treatment composition comprises at least one carboxylic acid chosen from oxalic acid and malic acid, and optionally at least one additional carboxylic acid. In further embodiments, the treatment composition comprises at least one carboxylic acid other than maleic acid. In still further embodiments, the treatment composition is free or substantially free of maleic acid.

The at least one carboxylic acid may be present in the treatment composition in an amount up to about 50%, such as up to about 45%, up to about 40%, up to about 35%, up to about 30%, up to about 29%, up to about 28%, up to about 27%, up to about 26%, up to about 25%, up to about 24%, up to about 23%, up to about 22%, up to about 21%, up to about 20%, up to about 19%, up to about 18%, up to about 17%, up to about 16%, up to about 15%, up to about 14%, up to about 13%, up to about 12%, up to about 11%, up to about 10%, up to about 9%, up to about 8%, up to about 7%, up to about 6%, up to about 5%, up to about 4%, up to about 3%, up to about 2%, up to about 1%, up to about 0.5%, or up to about 0.1% by weight, based on the weight of the treatment composition. By way of non-limiting example only, the at least one carboxylic acid may be present in an amount ranging from about 0.01% to about 30%, such as about 0.1% to about 25%, about 1% to about 20%, about 3% to about 15%, about 5% to about 14%, or about 10% to about 14% by weight, based on the weight of the treatment composition. In one exemplary embodiment, the at least one carboxylic acid may be present in an amount ranging from about 4% to about 25%, such as about 4% to about 10%, about 5% to about 8%, or about 6% to about 7% by weight, based on the weight of the treatment composition. In alternate embodiments, the at least one carboxylic acid may be present in an amount ranging from about 20% to about 30%, such as about 22% to about 28%, about 24% to about 26%, or about 24.5% to about 25.5% by weight. For example, the at least one carboxylic acid may be present in an amount ranging from about 5% to about 15%, about 8% to about 13%, such as about 8% to about 11%, about 8% to about 10%, about 9% to about 13%, about 9% to about 12%, about 9% to about 11%, about 10% to about 13%, about 10% to about 12%, about 10% to about 11%, about 11% to about 14%, about 11% to about 13%, about 12% to about 13%, about 20% to about 25%, about 21% to about 24%, about 22% to about 23%, such as about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight, based on the weight of the treatment composition. It should be understood that when more than one carboxylic acid is present, the total amount of carboxylic acids may be present in these amounts.

Solvent

The treatment composition may further comprise at least one solvent. In various exemplary and non-limiting embodiments, the solvent may be chosen from cosmetically acceptable solvents chosen from water, at least one cosmetically acceptable organic solvent, and mixtures thereof.

The organic solvents may be volatile or non-volatile compounds. As examples of organic solvents, non-limiting examples include monoalcohols and polyols such as ethanol, isopropyl alcohol, propyl alcohol, benzyl alcohol, and phenylethanol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerine.

The cosmetically acceptable solvent may comprise an amount ranging up to about 95%, such as up to about 90%, up to about 85%, up to about 80%, up to about 75%, up to about 70%, up to about 65%, up to about 60%, up to about 55%, or up to about 50%, by weight, based on the weight of the treatment composition. For example, the cosmetically acceptable solvent may range from about 65% to about 95% by weight, from about 70% to about 90% by weight, or from about 80% to about 85% by weight, or from about 5% to about 20% by weight, based on the weight of the treatment composition.

Additional components may optionally be present in the treatment composition. By way of example only, the treatment composition may comprise coloring agents (including but not limited to permanent, semi-permanent, or demi-permanent hair coloring agents), pH adjusters, emulsifiers, thickening agents and rheology modifying agents, cationic polymers, humectants and moisturizing agents, chelating agents such as glycine, emulsifying agents, fillers, structuring agents, propellants, anionic surfactants, cationic surfactants, amphoteric surfactants, shine agents, conditioning agents, and strengthening agents.

The pH of the treatment composition may range up to about 7, such as from about 1 to about 6, from about 1 to about 4, such as from about 2 to about 4, about 2.5 to about 3.5, or from about 2 to about 3.

The treatment composition may, in various embodiments, be applied onto the hair within about 24 hours, such as less than 24 hours or less than 12 hours, before or after a composition for altering the color or shape of the hair. In at least certain exemplary embodiments, the treatment composition may be applied to the hair within a few hours or a few minutes before or after the color- or shape-altering composition. For example, the treatment composition may be applied within about 1 to about 6 hours before or after the color- or shape-altering composition, or may be applied up to about 60 minutes, such as up to about 30 minutes, up to about 20 minutes, up to about 10 minutes, up to about 5 minutes, up to about 2 minutes, or up to about 1 minute before or after the color- or shape-altering composition.

In yet further embodiments, the treatment composition may be applied to the hair at the same time or substantially the same time as a color- or shape-altering composition. For example, the treatment composition may be mixed with a color- or shape-altering composition, or may be applied simultaneously with a color- or shape-altering composition. In various exemplary embodiments where the treatment composition is mixed with a color- or shape-altering composition, the pH of the resulting mixture may range, for example, from about 7 to about 12, such as about 8 to about 11, about 9 to about 11, or about 10 to about 11.

In still further embodiments, the treatment composition may be applied to the hair within about 24 hours, such as less than 24 hours or less than 12 hours, before or after a composition that is not a composition for altering the color or shape of the hair. In at least certain exemplary embodiments, the treatment composition may be applied to the hair within a few hours or a few minutes before or after the composition that is not a composition for altering the color or shape of the hair. For example, the treatment composition may be applied within about 1 to about 6 hours before or after the composition that is not a composition for altering the color or shape of the hair, or may be applied up to about 60 minutes, such as up to about 30 minutes, up to about 20 minutes, up to about 10 minutes, up to about 5 minutes, up to about 2 minutes, or up to about 1 minute before or after the composition that is not a composition for altering the color or shape of the hair.

In yet further embodiments, the treatment composition may be applied to the hair at the same time or substantially the same time as a hair composition that is not a color- or shape-altering composition. For example, the treatment composition may be mixed with a composition that is not a composition for altering the color or shape of the hair, or may be applied simultaneously with a composition for treating the hair.

In a still further embodiment, the treatment composition may be mixed with water and applied to the hair.

The treatment composition may be left on the hair for a period of time ranging up to one hour, such as from about 3 minutes to about 45 minutes, from about 5 minutes to about 30 minutes, or from about 10 minutes to about 20 minutes. In further embodiments, the treatment composition may be left on the hair for a period up to about 30 minutes, such as, for example, from about 1 to about 30 minutes, about 1 to about 10 minutes, or about 1 to about 5 minutes.

Exemplary Embodiments and Amounts of Components

According to various embodiments, the treatment composition may include 2-2AEE and a combination of carboxylic acids. By way of non-limiting example, the treatment composition may include 2-2AEE and a combination of two carboxylic acids, such as malonic acid and citric acid, malonic acid and oxalic acid, malonic acid and maleic acid, malonic acid and malic acid, citric acid and oxalic acid, citric acid and maleic acid, citric acid and malic acid, oxalic acid and maleic acid, oxalic acid and malic acid, maleic acid and malic acid, and so on. In other embodiments, the treatment composition may include 2-2AEE and combinations of three or more carboxylic acids.

In some embodiments, the treatment composition may include 2-2AEE and one or more saturated carboxylic acids, and may be free or substantially free of unsaturated carboxylic acids. In other embodiments, the treatment composition may include 2-2AEE and one or more unsaturated carboxylic acids and be free or substantially free of saturated carboxylic acids. In still other embodiments, the treatment composition may include 2-2AEE and both saturated (e.g. oxalic acid, malonic acid, glutaric acid, succinic acid, adipic acid, glycolic acid, citric acid, tartaric acid, malic acid, sebacic acid, glyoxylic acid monohydrate) and unsaturated (maleic acid, fumaric acid, benzoic acid, citraconic acid) carboxylic acids.

In some embodiments the treatment composition may include from about 5 wt % to about 15 wt % 2-2AEE, such as from about 6 wt % to about 13 wt %, from about 7 wt % to about 12 wt %, from about 8 wt % to about 11 wt %, or from about 9 wt % to about 10 wt % 2-2AEE. In various embodiments, the treatment composition may include from about 20 wt % to about 30 wt % oxalic acid or malic acid, such as from about 21 wt % to about 29 wt %, from about 22 wt % to about 28 wt %, from about 23 wt % to about 27 wt %, from about 24 wt % to about 26 wt %, or about 25 wt % oxalic acid or malic acid.

In various embodiments, the treatment composition may include from about 9 wt % to about 12 wt %, such as about 9 wt % to about 10 wt %, 2-2AEE, and from about 23 wt % to about 25.5 wt %, such as about 24 wt % to about 25 wt %, malic acid. In further embodiments, the treatment composition may include from about 9 wt % to about 12 wt %, such as about 9 wt % to about 10 wt %, 2-2AEE, and from about 5 wt % to about 8 wt %, such as about 6 wt % to about 7 wt %, oxalic acid.

According to certain embodiments, the total combined amount of 2-2AEE and carboxylic acid present in the treatment composition may range up to about 40%, such as up to about 35%, for example from about 15% to about 35%, from about 16% to about 33%, from about 17% to about 31%, or about 18% to about 30% by weight, based on the weight of the treatment composition.

Without intending to limit the disclosure, it may, in various embodiments, be advantageous to choose certain amounts of the 2-2AEE, at least one carboxylic acid, solvent, and/or optionally any additional component in the treatment composition, or ratios of the components in relation to one another, in order to provide or enhance synergistic results from the combinations thereof.

Color-Altering Composition

Before, after, or simultaneously with the treatment composition, a color-altering composition may be applied to the hair. In various exemplary embodiments, the color-altering composition may comprise an agent for bleaching the hair. For example, the color-altering composition may be formed by combining, in a cosmetically acceptable carrier, a bleach composition comprising at least one oxidizing agent chosen from persulfates, perborates, percarbonates, peracids, bromates, their salts and mixtures thereof, and a developer composition comprising hydrogen peroxide. In other embodiments, the oxidizing agent and developer may be separate. In yet further embodiments, the color-altering composition may comprise at least one colorant compound chosen from oxidative dye precursors, direct dyes, pigments, and mixtures thereof.

Bleaching Agent

According to various embodiments, the color-altering composition may comprise, in a cosmetically acceptable carrier, at least one oxidizing agent chosen from peroxides, persulfates, perborates, percarbonates, peracids, bromates, their salts and mixtures thereof. The at least one oxidizing agent may, optionally, be water-soluble.

Optional peroxides useful herein include, for example, hydrogen peroxide, magnesium peroxide, PVP-peroxide, calcium peroxide, and sodium peroxide.

Exemplary, non-limiting persulfates include potassium persulfate, sodium persulfate, and ammonium persulfate. In various embodiments, exemplary oxidizing agents may be chosen from sodium perborate and sodium percarbonate. In further embodiments, exemplary peracids may be chosen from organic peracids having the general formula (I):

R—C(O)OOH        (I)

wherein, in formula (I), R is chosen from saturated or unsaturated, substituted or unsubstituted, straight or branched chain, alkyl, aryl or alkaryl groups having from 1 to 22 carbon atoms. In at least some exemplary embodiments, mixtures of two or more oxidizing agents chosen from persulfates, perborates, percarbonates, peracids, bromates, and salts thereof, may be chosen.

In various embodiments, the at least one bleaching agent is chosen from alkali metal salts of perborates, percarbonates, bromates, and persulfates, such as, for example, ammonium, sodium, and potassium salts.

Bleach Composition

When the color-altering composition comprises separate bleach and developer compositions, the bleach composition may comprise at least one oxidizing agent chosen from persulfates, perborates, percarbonates, peracids, bromates, their salts, and mixtures thereof, such as those described above. In various embodiments, the at least one oxidizing agent is chosen from alkali metal salts of perborates, percarbonates, bromates, and persulfates, such as, for example, ammonium, sodium, and potassium salts. The bleach composition may also optionally comprise a cosmetically acceptable carrier.

The at least one oxidizing agent of the bleach compositions according to various embodiments of the disclosure is utilized in an amount sufficient to lighten or "bleach" hair. By way of example only, the at least one oxidizing agent of the bleach composition may be present in an amount ranging from about 10% by weight to about 100% by weight, such as from about 20% to about 90% by weight, from about 30% to about 80% by weight, or from about 40% to about 75% by weight, based on the total weight of the bleach composition. In further embodiments, the at least one oxidizing agent of the bleach composition may be present in an amount ranging from about 5% to about 50%, such as about 10% to about 45%, or about 15% to about 40%. In one exemplary embodiment, the at least one oxidizing agent of the bleach composition may be present in an amount of at least 40% by weight, based on the total weight of the bleach composition.

The bleach composition may be in any form, such as, for example, in the form of a powder, gel, liquid, foam, lotion, cream, mousse, and emulsion.

In various exemplary embodiments, the bleach composition may be anhydrous. Optionally, water may be added as an activator, by mixing it with the bleach composition.

The bleach composition of the present invention may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The pH adjusters may, in various embodiments, be present in the bleach composition in an amount effective to provide the color-altering composition with a pH ranging from about 1 to about 7 when the bleach composition is combined with the developer composition. By way of example, the amount of pH adjuster may be present, in various embodiments, in an amount of at least about 0.01%, such as at least about 0.1%, at least about 0.2%, or at least about 0.5%.

According to one exemplary embodiment, the bleach composition is alkaline, with the pH ranging from about 7, 8, 9, or 10 to about 8, 9, 10, or 11. According to a further exemplary embodiment, the bleach composition has a pH higher than about 7.

When the bleach composition is in powder form, the pH may be measured in a 1% solution in water.

Colorants may also optionally be present in the bleach compositions described herein. The colorants useful according to various embodiments of the disclosure are those colorants that are stable in the bleach composition, and can impart additional toning and coloring to hair. Exemplary hair colorants include, but are not limited to, pigments, liposoluble dyes, direct dyes, nacreous pigments, pearling agents, leuco dyes, optical lightening colorants, natural colorants and optically-variable pigments.

Developer Composition

When the color-altering composition comprises separate bleach and developer compositions, the developer composition comprises hydrogen peroxide. The developer composition may also optionally comprise a cosmetically acceptable carrier.

In various exemplary embodiments, hydrogen peroxide is present in an amount of at least about 1% by weight, based on the total weight of the developer composition. In further embodiments, hydrogen peroxide is present in an amount ranging from about 0.1% to about 80% by weight, such as from about 1.0% to about 75% by weight, or from about 2% to about 10% by weight, based on the total weight of the developer composition. In further exemplary embodiments, the hydrogen peroxide may be present in the developer composition in an amount ranging from about 2% to about 25%, such as about 4% to about 20%, about 6% to about 15%, or about 7% to about 10%.

The cosmetically acceptable carrier of the developer composition may, for example, be present in an amount ranging from about 0.5% to about 99% by weight, such as from about 5% to about 95% by weight, relative to the total weight of the developer composition.

The pH of the developer composition can range from about 1 to about 5, such as from about 2 to about 4, and it may be adjusted to the desired value using pH adjusters that are well known in the art in the cosmetic treatment of keratin fibers, including, for example, those described herein.

The developer composition may be in the form of a powder, gel, liquid, foam, lotion, cream, mousse, and emulsion.

According to various exemplary embodiments, the developer composition may be anhydrous. Optionally, water may be added as an activator, by mixing it with the developer composition.

The developer composition may, in various embodiments, comprise additional components such as, for example, at least one auxiliary ingredient chosen from rheology-modifying agents, chelating agents, fatty substances, ceramides, alkoxyaminosilicones, and silanes, and any other component known in the art to be useful in a developer composition.

In at least one exemplary embodiment, the bleach composition may be mixed with the developer composition to form the color-altering composition right before (e.g. within a few minutes before) applying the color-altering composition onto the hair.

In one exemplary embodiment, the bleach composition and developer composition may be combined to form the lightening composition in a ratio of bleach composition to developer composition ranging from about 1:1 to about 1:5, such as from about 1:1 to about 1:2, or about 1:2 to about 1:4.

Coloring Compounds

As described herein, in various exemplary and non-limiting embodiments, color-altering compositions may optionally comprise at least one colorant compound chosen from oxidation dyes, direct dyes, pigments, and mixtures thereof.

The oxidation dyes are generally chosen from one or more oxidation bases optionally combined with one or more couplers.

By way of example, the oxidation bases may be chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases can include the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethy)amino]ethanol, 2-[(3-aminopyrazolo[1,5-a]pyrid-7-yl)(2-hydroxyethy)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-☐-hydroxyethoxy-3-amino-pyrazolo[1,5-a]pyridine; 2-(4-diméthylpyperazinium-1-yl)-3-amino-pyrazolo[1,5-a]pyridine; and the addition salts thereof.

More particularly, oxidation bases can be selected from 3-aminopyrazolo-[1,5-a]-pyridines and preferably substituted on carbon atom 2 by:
(a) one (di)($C_1$-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatomes, potentially cationic, potentially substituted by one or more ($C_1$-$C_6$) alkyl, such as di($C_1$-$C_4$)alkylpipèrazinium; or
(c) one ($C_1$-$C_6$)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazino-pyrazole, 1-benzyl-4,5-diamino-3-methylpyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Compositions may optionally further comprise one or more couplers advantageously chosen from those conventionally used in the dyeing or coloring of keratinous substrates.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(ß-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methylbenzene, 4-chloro-1,3-dihydroxybenzene, 2,4-diamino-1-(ß-hydroxyethyloxy)benzene, 2-amino-4-(ß-hydroxy-ethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-ß-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzo-morpholine, 3,5-diamino-2,6-dimethoxypyridine, 1-N-(ß-hydroxyethyl)amino-3,4-methylenedioxybenzene, 2,6-bis(ß-hydroxyethylamino)toluene, 6-hydroxyindoline, 2,6-dihydroxy-4- methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methyl-pyrazolo[1,5-a]benzimidazole, the addition salts thereof with an acid, and mixtures thereof.

In general, the addition salts of the oxidation bases and couplers that may be used are chosen from the addition salts with an acid such as the hydrochlorides, hydrobromides, sulfates, citrates, succinates, tartrates, lactates, tosylates, benzenesulfonates, phosphates and acetates.

The oxidation base(s) may be present in an amount ranging from about 0.001% to 10% by weight, such as from about 0.005% to 5% by weight, relative to the total weight of the composition comprising the system in which it is present.

The coupler(s), if they are present, may be present in an amount ranging from about 0.001% to 10% by weight, such as from about 0.005% to 5% by weight, relative to the total weight of the system or composition comprising the system in which it is present.

Compositions according to embodiments of the disclosure may optionally comprise one or more synthetic or natural direct dyes, for example chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Preferably direct dyes are cationic direct dyes. Mention may be made of the hydrazono cationic dyes of formulas (Va) and (V'a), the azo cationic dyes (VIa) and (VI'a) and the diazo cationic dyes (VIIa) below:

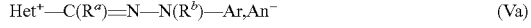
$$Het^+-C(R^a)=N-N(R^b)-Ar,An^- \quad (Va)$$

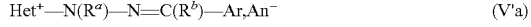
$$Het^+-N(R^a)-N=C(R^b)-Ar,An^- \quad (V'a)$$

$$Het^+-N=N-Ar,An^- \quad (VIa)$$

$$Ar^+-N=N-Ar'',An^- \quad (VI'a) \text{ and}$$

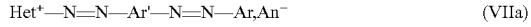
$$Het^+-N=N-Ar'-N=N-Ar,An^- \quad (VIIa)$$

in which formulas (Va), (V'a), (VIa), (VI'a) and (VIIa):

Het$^+$ represents a cationic heteroaryl moiety, preferably bearing an endocyclic cationic charge, such as imidazolium, indolium or pyridinium, optionally substituted preferentially with one or more $(C_1-C_8)$ alkyl groups such as methyl;

Ar$^+$ representing an aryl moiety, such as phenyl or naphthyl, bearing an exocyclic cationic charge, preferentially ammonium, particularly tri$(C_1-C_8)$alkylammonium such as trimethylammonium;

Ar represents an aryl group, especially phenyl, which is optionally substituted, preferentially with one or more electron-donating groups such as i) optionally substituted $(C_1-C_8)$alkyl, ii) optionally substituted $(C_1-C_8)$ alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$alkoxy;

Ar" is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

$R^a$ and $R^b$, which may be identical or different, represent a hydrogen atom or a group $(C_1-C_8)$alkyl, which is optionally substituted, preferentially with a hydroxyl group; or alternatively the substituent $R^a$ with a substituent of Het$^+$ and/or $R^b$ with a substituent of Ar and/or $R^a$ with $R^b$ form, together with the atoms that bear them, a (hetero)cycloalkyl;

particularly, $R^a$ and $R^b$ represent a hydrogen atom or a group $(C_1-C_4)$alkyl, which is optionally substituted with a hydroxyl group;

An$^-$ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly mention may be made of those of formulae (Va), (V'a) and (VIa) derived from the dyes described in patent applications WO 95/15144, WO 95/01772 and EP-714954.

In various embodiments, the cationic part is derived from the following derivatives:

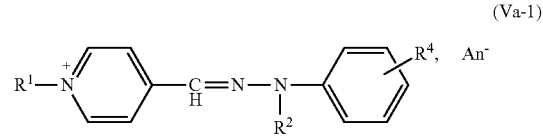

(Va-1)

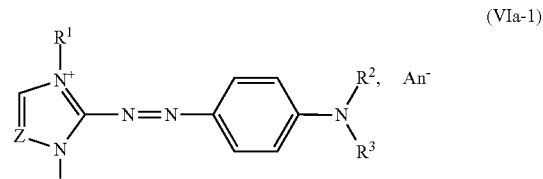

(VIa-1)

wherein in formulae (Va-1) and (VIa-1):

R$^1$ representing a $(C_1-C_4)$ alkyl group such as methyl;

R$^2$ and R$^3$, which are identical or different, represent a hydrogen atom or a $(C_1-C_4)$alkyl group, such as methyl; and R$^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group (s) with a hydroxyl group; particularly, R$^4$ is a hydrogen atom, Z represents a CH group or a nitrogen atom, preferentially CH;

An$^-$ represents an anionic counter-ion such as mesylate or halide.

The dye of formulae (Va-1) and (VIa-1) can be chosen from Basic Red 51, Basic Yellow 87 and Basic Orange 31 or derivatives thereof:

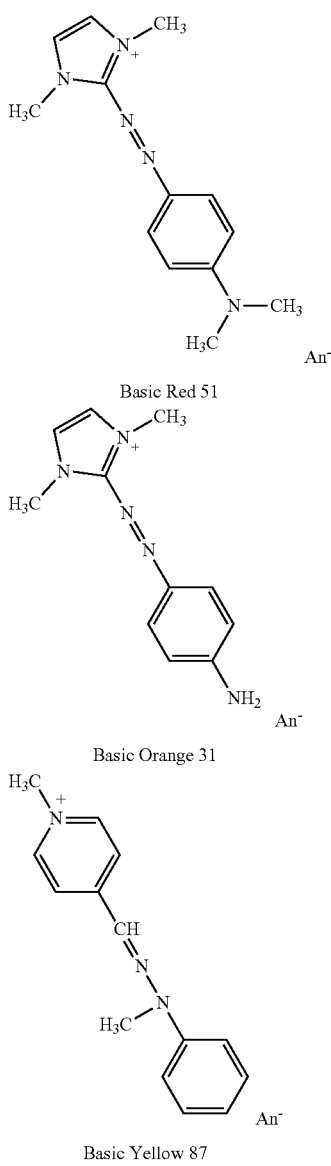

Basic Red 51

Basic Orange 31

Basic Yellow 87

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the one or more direct dyes more particularly represent from about 0.001% to 10% by weight, such as from about 0.005% to 5% by weight, of the total weight of the system or composition comprising the system in which it is present.

The color-altering composition may also comprise a cosmetically acceptable carrier. The cosmetically acceptable carrier may, for example, be present in the color-altering composition in an amount ranging from about 1% to about 40% by weight, such as from about 5% to about 35% by weight, or about 10% to about 30% by weight of the color-altering composition.

Auxiliary ingredients may be added to the color-altering composition. Exemplary auxiliary ingredients useful in the color-altering composition according to various embodiments of the disclosure include, but are not limited to, rheology-modifying agents, bleach activators and co-bleach activators, direct dyes, chelants, fatty substances, ceramides, alkoxyaminosilicones, silanes, and lift-enhancing agents, such as nitrogen-containing compounds and metal catalyst compounds.

The color-altering composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The pH adjusters may, in various embodiments, be present in the color-altering composition in an amount effective to provide the color-altering composition with a pH of not greater than 7, such as a pH ranging from about 1 to about 7, from about 2 to about 6, or from about 3 to about 5. By way of example, the amount of pH adjuster may be present, in various embodiments, in an amount of at least about 0.01%, such as at least about 0.1%, at least about 0.2%, or at least about 0.5%.

The color-altering composition may, in at least certain embodiments, be in a ready-to-use form.

The color-altering composition may, in various embodiments, be applied onto the hair within about 24 hours, such as less than 24 hours or less than 12 hours, after the treatment composition. In at least certain exemplary embodiments, the color-altering composition may be applied to the hair within a few hours or a few minutes after the treatment composition. For example, the color-altering composition may be applied within about 1 to about 6 hours after the treatment composition, or may be applied up to about 60 minutes, such as up to about 30 minutes, up to about 20 minutes, up to about 10 minutes, up to about 5 minutes, up to about 2 minutes, or up to about 1 minute after the treatment composition.

The color-altering composition may be left on the hair for a period of time sufficient to achieve the desired alteration in hair tone. For example, the color-altering composition may be left on the hair for up to one hour, such as from about 3 minutes to about 45 minutes, from about 5 minutes to about 30 minutes, or from about 10 minutes to about 20 minutes. In further embodiments, the color-altering composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the color-altering composition on the hair in order to achieve the desired alternation in hair tone. By way of non-limiting example, various embodiments according to the disclosure may provide for an increase of 1 to 4 in the tone height of the hair.

If desired, the color-altering composition may, optionally, be shampooed and/or rinsed off the hair.

Shape-Altering Composition

In further embodiments, a composition for shaping or altering the shape of the hair may be applied to the hair before, after, or simultaneously with the treatment composition. Compositions for altering the shape of the hair comprise hair shaping agents and may be any composition for altering the shape of the hair, for example compositions comprising one or more agents for straightening, relaxing, and/or shaping the hair.

By way of example, hair shaping agents may optionally be chosen from inorganic hydroxides or organic hydroxides, for example sodium hydroxide, potassium hydroxide, lithium hydroxide, calcium hydroxide, or guanidine hydroxide, or may be chosen from organic amines and other non-hydroxide compounds. In various embodiments, the hair relaxing agents may be chosen from thiol compounds such as cysteine, cysteamine, N-substituted cysteamines, alkyl substituted mercaptoacetamides, dimercaptoadipic acid, thioglycerol, thiolactic acid, thioglycolic acid or its salts; (e.g., a thioglycolate), monothioglycolic acid esters such as diol esters of thioglycolic acid, glyceryl monothioglycolate, thiocholine or its salts, amino thiols, and thiols attached to low molecular weight polymers, sulfites such as sodium hyposulfite, and bisulfites such as ammonium or sodium bisulfite.

The compositions for altering the shape of the hair may optionally comprise at least one surfactant, for example amphoteric/zwitterionic surfactants, nonionic surfactants, anionic surfactants, and cationic surfactants. By way of non-limiting example, the at least one surfactant may be present in an amount ranging from about 0.1% to about 5% by weight, such as from about 0.5% to about 3% by weight, based on the total weight of the shape-altering composition.

Exemplary amphoteric surfactants include, for example, lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, and cocoamphopropylsulfonate, and combinations thereof.

Exemplary nonionic surfactants include fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides such as PEG-15 cocamide; amine oxides, such as cocamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as nonoxynol, and combinations thereof.

Exemplary anionic surfactants include, alkylethercarboxylic acids, such as laureth-11 carboxylic acid, the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about C.sub.12 to C.sub.18 alkyl or alkenyl groups, and combinations thereof. Particular examples include the salts of lauryl sulfates and lauryl ether sulfates, the latter having an average level of ethoxylation of 1-3.

Exemplary cationic surfactants include quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and combinations thereof.

Hair shaping compositions may further contain at least one additional ingredient typically found in such compositions. Examples of such ingredients include, but are not limited to, acid and alkali pH adjusting agents, chelating agents, swelling agents, solvents, structuring agents such as waxes and polymers, hydrophobic (lipophilic) and hydrophilic thickeners or gelling agents, skin conditioning agents, sunscreen agents (e.g., octocrylene, octinoxate, avobenzone), preservatives (e.g., sodium citrate, phenoxyethanol, parabens and mixtures thereof), cosmetic active agents and dermatological active agents such as, for example, hydrolyzed peptides, farnesol, bisabolol, phytantriol, aesthetic agents such as essential oils, fragrances, skin sensates, opacifiers, aromatic compounds (e.g., clove oil, menthol, camphor, *eucalyptus* oil, and eugenol), foam enhancers, and botanical extracts.

The hair shaping composition may also comprise a cosmetically acceptable carrier. The cosmetically acceptable carrier may, for example, be present in the shape-altering composition in an amount ranging from about 1% to about 40% by weight, such as from about 5% to about 35% by weight, or about 10% to about 30% by weight of the shape-altering composition.

In various embodiments, the hair shaping composition comprises or is used in conjunction with at least one neutralizer, for example an oxidizing agent. Exemplary useful oxidizing agents include peroxides, bromates, and perborates, e.g., hydrogen peroxide, potassium bromate, sodium bromate and sodium perborate.

The hair shaping composition may, in various embodiments, be applied onto the hair within about 24 hours, such as less than 24 hours or less than 12 hours, after the treatment composition. In at least certain exemplary embodiments, the shape-altering composition may be applied to the hair within a few hours or a few minutes after the treatment composition. For example, the shape-altering composition may be applied within about 1 to about 6 hours after the treatment composition, or may be applied up to about 60 minutes, such as up to about 30 minutes, up to about 20 minutes, up to about 10 minutes, up to about 5 minutes, up to about 2 minutes, or up to about 1 minute after the treatment composition.

The shape-altering composition may be left on the hair for a period of time sufficient to achieve the desired alteration in hair shape. For example, the shape-altering composition may be left on the hair for up to one hour, such as from about 3 minutes to about 45 minutes, from about 5 minutes to about 30 minutes, or from about 10 minutes to about 20 minutes. In further embodiments, the shape-altering composition may be left on the hair for a period up to about 30 minutes, such as, for example, from about 1 to about 30 minutes, about 1 to about 10 minutes, or about 1 to about 5 minutes. One skilled in the art will, by considering various factors such as starting hair shape and desired hair shape, be able to determine an appropriate amount of time to leave the shape-altering composition on the hair in order to achieve the desired alternation in hair shape.

If desired, the shape-altering composition may, optionally, be shampooed and/or rinsed off the hair.

Conditioning Composition

After the treatment composition and/or color-altering composition and/or shape-altering composition have been applied to the hair, and optionally shampooed and/or rinsed, the hair may be further treated with a conditioning composition comprising 2-(2-aminoethoxy)ethanol and at least one carboxylic acid. In various non-limiting exemplary embodiments, the 2-(2-aminoethoxy)ethanol may be neutralized by the at least one carboxylic acid. As used herein, the 2-(2-aminoethoxy)ethanol being neutralized with the at least one carboxylic acid means that the 2-(2-aminoethoxy)ethanol is completely neutralized, is substantially completely neutralized, or is partially neutralized. The term "neutralized" means that the 2-(2-aminoethoxy)ethanol is protonated by $H^+$ (proton) coming from, but not limited to, acidic sources such as the carboxylic acid(s).

In various embodiments, the 2-(2-aminoethoxy)ethanol may be present in the conditioning composition in an amount up to about 10%, such as up to about 9%, up to about 8%, up to about 7%, up to about 6%, up to about 5%, up to about 4%, up to about 3%, up to about 2%, up to about 1%, up to about 0.90%, up to about 0.80%, up to about 0.70%, up to about 0.60%, or up to about 0.50% by weight, based on the weight of the conditioning composition. By way of non-limiting example only, the 2-(2-aminoethoxy)ethanol may be present in an amount ranging from about 0.1% to about 5%, such as about 0.2% to about 4%, or about 1% to about 3% by weight, based on the weight of the conditioning composition. In one embodiment, the 2-(2-aminoethoxy)ethanol may be present in an amount ranging from about 2% to about 3% by weight, based on the weight of the conditioning composition.

The at least one carboxylic acid useful for the conditioning composition may be any organic compound containing at least one acid functional group and at least one carbon atom, such as the carboxylic acids described above for the treatment composition. Exemplary and non-limiting carboxylic acids that may be used include organic compounds that include, for example, one, two, three, or more carboxylic acid functional groups (COOH) and at least one carbon atom.

In certain exemplary, and non-limiting embodiments, the at least one carboxylic acid may be chosen from saturated or unsaturated, substituted or unsubstituted dicarboxylic acids, salts thereof, and mixtures thereof. By way of non-limiting example, the at least one carboxylic acid may be chosen from dicarboxylic acids of the following formula:

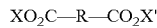

wherein:
- —R is a cyclic or acyclic, saturated or unsaturated, linear or branched, $C_1$-$C_{100}$ hydrocarbon moiety comprising from 0 to 30 double and/or triple bonds and/or from 0 to 10 rings, and optionally interrupted by 1 to 30 heteroatoms chosen from O, N and S, and optionally substituted with 1 to 30 substituents chosen from a hydrogen atom, a hydroxyl (—OH) moiety, an amino (—$NH_2$) moiety, a ($C_1$-$C_{30}$)alkylamino moiety, a poly($C_1$-$C_{30}$)alkylamino moiety, a hydroxy($C_1$-$C_{30}$)alkylamino moiety, a polyhydroxy($C_1$-$C_{30}$)alkylamino moiety, a $C_6$-$C_{30}$ aryl moiety, and in some embodiments —R may be omitted,
- —X and X', independently denote a hydrogen atom, an ammonium ion, a ion of an alkali metal such as Li, Na, K, or an alkaline earth metal such as Be, Mg, Ca or an ion derived from an organic amine such as an alkylamine.

It is understood that the expression cyclic hydrocarbon moiety for the purposes of the present application is understood to mean a hydrocarbon moiety consisting of one or more rings or comprising one or more rings which are pendent or in the principle chain, it being possible for the rings to be saturated or unsaturated and to be substituted with one or more $C_1$-$C_{30}$ alkyl or alkenyl or hydroxyl or amino moieties.

By way of non-limiting example only, carboxylic acids useful in the conditioning composition may include oxalic acid, malonic acid, malic acid, glutaric acid, citraconic acid, citric acid, maleic acid, glycolic acid, succinic acid, adipic acid, tartaric acid, fumaric acid, sebacic acid, benzoic acid, and glyoxylic acid monohydrate, as well as combinations thereof. In at least one embodiment, the conditioning composition comprises at least one carboxylic acid other than maleic acid.

It should be noted, however, that the carboxylic acid chosen for the conditioning composition may be the same as or different from the at least one carboxylic acid chosen for the treatment composition. In at least one embodiment, the conditioning composition comprises maleic acid and optionally at least one additional carboxylic acid. In further embodiments, the conditioning composition comprises at least one carboxylic acid other than maleic acid. In further embodiments, the conditioning composition is free or substantially free of maleic acid.

The at least one carboxylic acid may be present in the conditioning composition in an amount up to about 10%, such as up to about 9%, up to about 8%, up to about 7%, up to about 6%, up to about 5%, up to about 4%, up to about 3%, up to about 2%, up to about 1%, or up to about 0.50% by weight, based on the weight of the conditioning composition. By way of non-limiting example only, the carboxylic acid may be present in an amount ranging from about 0.50% to about 10%, such as about 1% to about 8%, about 2% to about 7%, about 3% to about 6%, or about 4% to about 5% by weight, based on the weight of the conditioning composition. In one exemplary embodiment, the carboxylic acid may be present in an amount of about 6% to about 8% by weight, based on the weight of the conditioning composition. It should be understood that when more than one carboxylic acid is present, the total amount of carboxylic acids may be present in these amounts.

The conditioning composition may, in various embodiments, be in the form of an emulsion, and may optionally comprise additional components, for example surfactants, solvents, and/or conditioning agents, as well as other additives.

By way of non-limiting example, the solvent may be chosen from cosmetically acceptable solvents chosen from water, at least one cosmetically acceptable organic solvent, and mixtures thereof.

The organic solvents may be volatile or non-volatile compounds. As examples of organic solvents, non-limiting mentions can be made of monoalcohols and polyols such as ethanol, isopropyl alcohol, propyl alcohol, benzyl alcohol, and phenylethanol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerine.

The cosmetically acceptable solvent may comprise an amount ranging up to about 98%, such as up to about 95%, up to about 90%, up to about 85%, up to about 80%, up to about 75%, up to about 70%, up to about 65%, up to about 60%, up to about 55%, or up to about 50%, by weight, based on the weight of the conditioning composition. For example, the cosmetically acceptable solvent may range from about 80% to about 98% by weight, such as from about 85% to about 95% by weight by weight, based on the weight of the conditioning composition.

Conditioning agents that may be included in the conditioning composition include, but are not limited to, cationic, anionic, non-ionic, and amphoteric conditioning agents. For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

Amphoteric conditioning agents may be chosen from polyquaternium-22, polyquaternium-39, polyquaternium-47, polyquaternium-53, arginine, asparagines, aspartic acid, glycine, glutamic acid, lysine, methionine, phenylalanine, serine, threonine, tyrosine, tryptophan, valine, gelatin, Quaternium-27, oleamidopropyl betaine, disodium cocoamphodiacetate, disodium cocoamphodipropionate, disodium lauroamphodiacetate, sodium cocoamphopropionate, sodium cocoamphoacetate, meadowfoam delta lactone, cocoamidopropyl betaine, cocoamidopropyl hydroxysultaine, lauramidopropyl betaine, carnitine, hydroxyproline, acetyl hydroxy proline, isoleucine, lauroyl lysine, lauroyl sarcosine, polylysine, proline, rice amino acids, silk amino acids, and wheat amino acids.

Additional auxiliary components that may be present in the conditioning composition include but are not limited to emulsifiers, thickening agents and rheology modifying agents, cationic polymers, humectants and moisturizing agents, chelating agents such as glycine, emulsifying agents other than those that fall under the above-described fatty substances, fillers, structuring agents, propellants, anionic surfactants, cationic surfactants, amphoteric surfactants, shine agents, conditioning agents, shine agents, and strengthening agents.

If present, the at least one auxiliary component may be present in an amount up to about 25%, such as up to about 20%, up to about 15%, or up to about 10% by weight, such as from about 0.1% to about 10% by weight, from about 0.5% to about 5%, or about 1 to about 3% by weight, based on the total weight of the conditioning composition.

The pH of the conditioning composition can range from about 1 to about 7, such as from about 2 to about 5, or about 3 to about 4.

According to various embodiments, the conditioning composition may include 2-2AEE and a combination of carboxylic acids. By way of non-limiting example, the conditioning composition may include 2-2AEE and a combination of two carboxylic acids, such as malonic acid and citric acid, malonic acid and oxalic acid, malonic acid and maleic acid, malonic acid and malic acid, citric acid and oxalic acid, citric acid and maleic acid, citric acid and malic acid, oxalic acid and maleic acid, oxalic acid and malic acid, maleic acid and malic acid, and so on. In other embodiments, the conditioning composition may include 2-2AEE and combinations of three or more carboxylic acids.

In some embodiments, the conditioning composition may include 2-2AEE and one or more saturated carboxylic acids and may be free or substantially free of unsaturated carboxylic acids. In other embodiments, the conditioning composition may include 2-2AEE and one or more unsaturated carboxylic acids and be free or substantially free of saturated carboxylic acids. In still other embodiments, the conditioning composition may include 2-2AEE and both saturated (e.g. oxalic acid, malonic acid, glutaric acid, succinic acid, adipic acid, glycolic acid, citric acid, tartaric acid, malic acid, sebacic acid, glyoxylic acid monohydrate) and unsaturated (maleic acid, fumaric acid, benzoic acid, citraconic acid) carboxylic acids.

In certain exemplary embodiments, the conditioning composition may include up to about 5 wt %, such as from about 0.1 wt % to about 5 wt % 2-2AEE, from about 0.5 wt % to about 3 wt %, or from about 0.5 wt % to about 2 wt % 2-2AEE, such as about 0.5 wt % to about 1 wt %, based on the weight of the conditioning composition. In certain exemplary embodiments, the conditioning composition may include from about 0.1 wt % to about 5 wt % carboxylic acids, such as from about 0.5 wt % to about 4 wt %, or from about 0.75 wt % to about 3 wt %, such as about 1 wt % to about 2 wt % carboxylic acids, based on the weight of the conditioning composition.

By way of non-limiting example only, the conditioning composition may include from about 0.5 wt % to about 2 wt % 2-2AEE and from about 0.75 wt % to about 3 wt % of one or more carboxylic acids, such as from about 0.5 wt % to about 1 wt % 2-2AEE and from about 1 wt % to about 2 wt % of one or more carboxylic acids, based on the weight of the conditioning composition. By way of non-limiting example, the conditioning composition may include from about 5 wt % to about 6 wt % 2-2AEE and from about 1 wt % to about 2 wt % malonic, citric, malic, and/or maleic acid, based on the weight of the conditioning composition.

According to certain embodiments, the total combined amount of 2-2AEE and carboxylic acid present in the conditioning composition may range up to about 20%, such as from about 0.5% to about 15%, from about 1% to about 15%, about 1% to about 10%, about 2% to about 8%, about 2% to about 5%, or about 3% to about 5% by weight, based on the weight of the conditioning composition.

Without intending to limit the disclosure, it may, in various embodiments, be advantageous to choose certain amounts of the 2-2AEE, at least one carboxylic acid, solvent, and/or optionally any additional component in the conditioning composition, or ratios of the components in relation to one another, in order to provide or enhance synergistic results from the combinations thereof.

The treatment and/or conditioning compositions according to the disclosure can be in various forms, such as in the form of liquids, creams, liquid-gels, liquid-creams, gels, lotions, or pastes.

Methods

As described herein, the treatment and/or conditioning compositions, and/or the systems comprising the treatment and conditioning compositions, may be used to treat the hair, for example before, during, and/or after a process to chemically alter the color or shape of hair, before, during, and/or after application of a composition that is not a color- or shape-altering composition, and/or as a stand-alone treatment for damaged hair. For example, a color- or shape-altering composition may comprise the treatment composition, or the treatment composition may comprise a color- or shape-altering composition or agent or composition. It should be understood that when "a color-altering composition comprises the treatment composition," "a shape-altering composition comprises the treatment composition," "the treatment composition comprises a color-altering composition," "the treatment composition comprises a shape-altering composition," or the like, the two compositions or their components are mixed together, but without any limitation, for example on which composition is added to which or the order of mixing.

In further embodiments, the treatment composition may be applied to the hair first, and optionally shampooed and/or rinsed, after which a color- or shape-altering composition, or composition that is not a color- or shape-altering composition, is applied to the hair. In various embodiments, the conditioning composition may be applied to the hair after the treatment composition and/or color- or shape-altering composition are applied to the hair, and optionally shampooed and/or rinsed.

As used herein, treatment compositions may be applied to the hair "before" chemical treatment of the hair, such as before shaping, coloring, or lightening the hair, with or without shampooing or rinsing in between, such as less than one minute before, up to about 5 minutes before, up to about 10 minutes before, up to about 20 minutes before, up to about 30 minutes before, up to about 1 hour before, up to about 2 hours before, up to about 6 hours before, up to about 12 hours before, up to about 24 hours before, up to about 48 hours before, up to about 72 hours before, or up to about 1 week before, for example.

As used herein, treatment compositions may be applied to the hair "after" chemical treatment of the hair, such as after shaping, coloring, or lightening the hair, with or without shampooing or rinsing in between, such as less than one minute after, up to about 5 minutes after, up to about 10 minutes after, up to about 20 minutes after, up to about 30 minutes after, up to about 1 hour after, up to about 2 hours after, up to about 6 hours after, up to about 12 hours after, up to about 24 hours after, up to about 48 hours after, up to about 72 hours after, or up to about 1 week after, for example.

As used herein, treatment compositions may be applied to the hair "during" chemical treatment of the hair, for example simultaneously with or at approximately the same time as chemical treatment such as shaping, coloring, or lightening the hair, for example by combining or mixing the treatment composition with the chemical treatment composition prior to application of the mixture to the hair. By way of example, the treatment compositions may be mixed with a color- or shape-altering composition at an amount ranging up to about 30% by weight, relative to the weight of the color-altering composition, such as up to about 25%, up to about 20%, or up to about 15% by weight, relative to the weight of the color-altering composition. For example, the treatment composition may be mixed with a color- or shape-altering composition at an amount ranging from about 1% to about 20%, about 2% to about 15%, about 3% to about 13%, or about 4% to about 10% by weight, relative to the weight of the color-altering composition. In yet further exemplary embodiments, the treatment composition and color- or shape-altering composition may be applied to the hair at substantially the same time, but from separate applicators without mixing prior to application to the hair, either with or without shampooing or rinsing in between.

By way of non-limiting example, a method for treating or altering the shape or color of the hair may comprise applying the treatment composition onto the hair as a pre-relaxing, pre-permanent waving, pre-straightening, pre-coloring, pre-glazing, or pre-lightening composition, which may optionally be left on the hair or washed out before application of the color- or shape-altering composition. In a further exemplary embodiment, a method may comprise adding the treatment composition into a color- or shape-altering composition, optionally just prior to use, and applying the mixture to the hair. In yet a further exemplary embodiment, a method may comprise adding a shape- or color-altering agent, for example an oxidizing agent or a dye, into the treatment composition, optionally just prior to use, and applying the treatment composition to the hair. In yet a further exemplary embodiment, a method may comprise mixing a shaping agent or colorant or bleach composition and developer just prior to use, wherein the treatment composition may be pre-formulated into the shaping or coloring or bleach composition, or developer composition. In yet a further exemplary embodiment, a method may comprise applying the conditioning composition onto the hair as a post-treatment composition after the hair has been treated and after optionally rinsing or washing the hair.

The term "mix" and all variations of this term as used herein refers to contacting or combining or reconstituting or dissolving or dispersing or blending or shaking the treatment composition with the shape- or color-altering composition. It can also mean introducing the treatment composition to the shape- or color-altering composition. It may also mean placing the treatment composition in the same vessel or container as the color-altering composition.

As a further example, a treatment composition according to the disclosure may be applied to the hair following the reducing step of a hair treatment process, e.g. a relaxer, straightener, or permanent wave. After an optional leave-in (processing) time, e.g. about 5-20 minutes, such as about 10-15 minutes, The hair may optionally be blotted or rinsed, and then the conditioning composition applied to the hair, and optionally shampooed and/or rinsed. Without wishing to be bound by theory, it is believed that the reducing step of the process swells the hair cuticle, rendering it able to accept active component(s) from the treatment composition, and the conditioning composition then de-swells the hair cuticle, sealing in the active component(s).

In yet further exemplary embodiments, the treatment composition, the conditioning composition, or systems comprising the treatment composition and the conditioning composition, may be applied to the hair not in conjunction with a color-altering or shape-altering composition or process. Such treatment compositions, conditioning compositions, and/or systems comprising the treatment composition and the conditioning composition may be useful to provide cosmetic advantages such as shine, conditioning, fiber strength, and/or a healthy appearance to the hair, separate and apart from avoiding or minimizing damage to the hair caused by chemical processes such as coloring, bleaching, shaping, relaxing, etc., the hair.

By way of non-limiting example only, a treatment composition according to the disclosure may be mixed with a composition that does not contain an agent for altering the color or shape of the hair, may be applied directly to the hair, for example simultaneously with a composition that does not contain an agent for altering the color or shape of the hair, or may be mixed with water and applied to the hair, and optionally the hair may be shampooed and/or rinsed, after which a conditioning composition.

In a further exemplary embodiment, methods relate to processes for treating the hair where only a portion of hair is subjected to a chemical process such as a color- or shape-altering process. By way of example, when hair is highlighted, only certain portions of hair on the head of a consumer are treated with a bleaching or highlighting agent. However, different portions of hair may be treated (e.g. highlighted) during subsequent color- or shape-altering processes, thus causing more damage to certain portions of the hair over time. Thus, it may be desirable in such embodiments to treat the entire head of hair with a treatment composition according to the disclosure. As such, in various embodiments, a treatment composition according to the disclosure may be applied to certain portions of the hair in conjunction with a bleaching or highlighting or hair dyeing or shaping process (e.g. mixed with a bleaching or highlighting or hair dyeing or shaping composition), while a treatment composition according to the disclosure may be applied to other portions of the hair that are not subjected to the chemical process, for example in a composition not containing an agent coloring or shaping the hair. Although some overlap of treated portions of the hair may occur, various embodiments contemplate that the treated hair will consist essentially of different portions of the hair.

Accordingly, methods of altering the color or shape of the hair are within the scope of the disclosure wherein a first treatment composition comprising 2-(2-aminoethoxy)ethanol; at least one carboxylic acid chosen from oxalic acid, malonic acid, malic acid, glutaric acid, citraconic acid, citric acid, glycolic acid, succinic acid, adipic acid, tartaric acid, fumaric acid, maleic acid, sebacic acid, benzoic acid, and glyoxylic acid monohydrate, and combinations thereof; at least one solvent; and at least one agent for altering the color or shape of the hair is applied to certain portions of hair; and a second treatment composition comprising 2-(2-aminoethoxy)ethanol; at least one carboxylic acid chosen from oxalic acid, malonic acid, malic acid, glutaric acid, citraconic acid, citric acid, glycolic acid, succinic acid, adipic acid, tartaric acid, fumaric acid, maleic acid, sebacic acid, benzoic acid, and glyoxylic acid monohydrate, and combinations thereof; and at least one solvent; wherein the second treatment composition does not contain an agent for altering the shape or color of the hair, is applied to different portions of hair. The second treatment composition may, for example, be applied directly to the hair, or may be mixed with water or a composition such as a clear glaze. Optionally, a conditioning composition according to the disclosure may also be applied to the hair, e.g. a portion of the hair or the entire treated hair. In various embodiments, it may be possible for the at least one carboxylic acid in the first and second treatment compositions and/or the conditioning composition to be the same or different, and the at least one carboxylic acid for each should be understood to be chosen independently.

In various exemplary methods or processes, the treatment composition or mixture comprising the treatment composition may be applied to the hair, and after an optional leave-on (processing) time on the hair fibers, for example, ranging from about 1 to about 60 minutes, such as from about 5 to about 50 minutes, or such as from about 5 to about 30 minutes, or such as from about 10 to about 20 minutes, or such as of about 20 minutes, the hair fibers may be rinsed, optionally washed with shampoo and rinsed again, the conditioning composition applied to the hair fibers, and after a second optional resting time, optionally washed with a hair conditioning composition, rinsed again, then dried. The conditioning composition may be left on the hair for a resting or leave-in period ranging up to about 60 minutes, such as from about 1 to about 30 minutes, or from about 5 to about 15 minutes. The shampoo and hair conditioning composition can be any conventional hair shampoo and/or conditioner products.

The temperature during the methods of treating the hair may be, for example, between room temperature and 80° C., such as between room temperature and 60° C., or between room temperature and 40° C.

It has been discovered that the application of the treatment composition, the conditioning composition, or a system comprising the treatment composition and conditioning composition onto the fibers, in conjunction with a process for altering the color and/or shape of the hair, results in satisfactory lifting or lightening of the color of the fibers, or alteration of the shape of the hair fibers, while providing strengthening and/or protection to the hair fiber, so as to minimize damage to the hair fiber in at least some embodiments. Additionally, when the embodiments of the composition comprise a colorant compound selected from oxidative dye precursors, direct dyes, pigments or their mixtures, the fibers are also colored satisfactorily with respect to degree of color deposit and desirable shade formation coloring, while providing strengthening and/or protection to the hair fiber, so as to avoid or minimize damage to the hair fiber in at least some embodiments.

It is to be understood that any degree of protection and/or strengthening and/or minimizing of damage may be imparted to the hair fiber, without limitation. In addition, it is intended that embodiments that do not impart fiber strength and/or protection and/or minimization of damage to the hair fiber are also within the scope of the disclosure.

Kits

Further embodiments of the disclosure relate to kits for treatment and/or altering the color and/or shape of the hair. One exemplary embodiment of a kit for treating and/or altering the color of hair comprises:

A. a first compartment containing a treatment composition comprising:
i. 2-(2-aminoethoxy)ethanol;
ii. at least one carboxylic acid; and
iii. optionally at least one solvent; and
B. a second compartment containing a conditioning composition comprising 2-2AEE neutralized by at least one carboxylic acid; and
C. optionally, one or more additional compartments comprising at least one hair coloring agent or composition.

Further exemplary embodiments of a kit for treating and/or altering the color of hair comprise:

A. a first compartment containing a treatment composition comprising:
i. 2-(2-aminoethoxy)ethanol;
ii. at least one carboxylic acid; and
iii. optionally at least one solvent; and
B. a second compartment containing a conditioning composition comprising 2-2AEE and at least one carboxylic acid; and C. optionally, one or more additional compartments comprising at least one hair coloring agent or composition, wherein the first and/or second compartments comprise at least one acid chosen from maleic acid, citric acid, malonic acid, or mixtures thereof.

An exemplary embodiment of a kit for treating and/or altering the shape of hair comprises:
A. a first compartment containing a treatment composition comprising:
i. 2-(2-aminoethoxy)ethanol;
ii. at least one carboxylic acid; and
iii. optionally at least one solvent; and
B. a second compartment containing a conditioning composition comprising 2-2AEE and at least one carboxylic acid; and
C. optionally, one or more additional compartments comprising at least one agent or composition for shaping the hair.

Further exemplary embodiments of a kit for treating and/or altering the shape of hair comprise:
A. a first compartment containing a treatment composition comprising:
i. 2-(2-aminoethoxy)ethanol;
ii. at least one carboxylic acid; and
iii. optionally at least one solvent; and
B. a second compartment containing a conditioning composition comprising 2-2AEE and at least one carboxylic acid; and
C. optionally, one or more additional compartments comprising at least one agent or composition for shaping the hair, wherein the first and/or second and/or compartments comprise at least one acid chosen from maleic acid, citric acid, malonic acid, or mixtures thereof. Further exemplary embodiments of a kit for treating and/or altering the shape of hair comprise:
A. a first compartment containing a treatment composition comprising:
i. 2-(2-aminoethoxy)ethanol;
ii. at least one carboxylic acid; and
iii. optionally at least one solvent; and
B. a second compartment containing a conditioning composition comprising 2-2AEE and at least one carboxylic acid; and
C. optionally, one or more additional compartments comprising at least one agent or composition for shaping the hair, wherein the first and/or second and/or one or more additional compartments are free or substantially free of maleic acid.

Further exemplary embodiments of a kit for treating and/or altering the shape of hair comprise:
A. a first compartment containing a treatment composition comprising:
i. 2-(2-aminoethoxy)ethanol;
ii. at least one carboxylic acid; and
iii. optionally at least one solvent; and
B. a second compartment containing a conditioning composition comprising 2-2AEE and at least one carboxylic acid; and
C. optionally, one or more additional compartments comprising at least one agent or composition for shaping the hair, wherein the first and/or second and/or compartments comprise at least one acid chosen from maleic acid, citric acid, or mixtures thereof.

According to various embodiments, the at least one carboxylic acid present in the hair treatment composition and/or the hair conditioning composition of any of the aforementioned kits may independently be chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, and glyoxylic acid monohydrate, and combinations thereof. In some embodiments, the at least one carboxylic acid in the treatment composition and the conditioning composition in the first and second compartments of the kit are the same. In other embodiments, the at least one carboxylic acid in the treatment composition and the conditioning composition in the first and second compartments of the kit are different.

In some embodiments, the at least one carboxylic acid present in the hair treatment composition and/or the hair conditioning composition in the first and second compartments of the kit are independently chosen from oxalic acid, malic acid, and combinations thereof. In further embodiments, the at least one carboxylic acid present in the hair treatment composition and/or the hair conditioning composition in the first and second compartments of the kit are independently chosen from citric acid, malonic acid, oxalic acid, malic acid, glutaric acid, glycolic acid, succinic acid, adipic acid, tartaric acid, sebacic acid, glyoxylic acid monohydrate, and combinations thereof. In yet further embodiments, the at least one carboxylic acid is chosen from maleic acid, citraconic acid, fumaric acid, benzoic acid, and combinations thereof. In still further embodiments, the carboxylic acid present in the treatment composition in the first compartment, the carboxylic acid present in the conditioning composition in the second compartment, or both, may be independently chosen from combinations of two carboxylic acids, chosen from: malonic acid and citric acid; malonic acid and oxalic acid; malonic acid and maleic acid; malonic acid and malic acid; citric acid and oxalic acid; citric acid and maleic acid; citric acid and malic acid; oxalic acid and maleic acid; oxalic acid and malic acid; and maleic acid and malic acid. In still further embodiments, the carboxylic acid present in the treatment composition in the first compartment, the carboxylic acid present in the conditioning composition in the second compartment, or both, may be independently chosen from combinations of three or more carboxylic acids.

In various exemplary and non-limiting embodiment, the at least one carboxylic acid present in the treatment composition in any of the aforementioned compositions, systems, methods, and kits is chosen from oxalic acid. In further exemplary and non-limiting embodiments, the at least one carboxylic acid present in the treatment composition in any of the aforementioned compositions, systems, methods, and kits is chosen from malic acid.

It to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

EXAMPLES

The ingredient amounts in the composition/formulations described below are expressed in % by weight, based on the total weight of the composition, unless otherwise indicated.

Examples 1-1 to 1-13

Compositions

The following exemplary treatment compositions comprising 2-(2-aminoethoxy)ethanol, at least one carboxylic acid, and at least one solvent were prepared. In Table 1, the amounts given are % by weight of the treatment composition, and the pH of each of the treatment compositions is approximately 3.0.

TABLE 1

| Formulation | Carboxylic Acid | Formula | Treatment Composition |
|---|---|---|---|
| 1-1 | Oxalic | | (11.28%) Oxalic acid<br>(18.68%) Ethanol<br>(14.63%) 2-(2-aminoethoxy)ethanol<br>(55.41%) DI water |
| 1-2 | Oxalic | | (8.27%) Oxalic acid<br>(18.66%) Ethanol<br>(11.29%) 2-(2-aminoethoxy)ethanol<br>(61.78%) DI water |
| 1-3 | Malonic | | (9.19%) Malonic Acid<br>(84.08%) DI Water<br>(6.73%) 2-(2-aminoethoxy)ethanol |
| 1-4 | Malic | | (12.38%) Malic Acid<br>(82.67%) DI Water<br>(4.94%) 2-(2-aminoethoxy)ethanol |
| 1-5 | Glutaric | | (87.92%) DI water<br>(12.072%) Glutaric acid<br>(0.0056%) 2-(2-aminoethoxy)ethanol |
| 1-6 | Citriconic | | (12.59%) Citraconic Acid<br>(78.86%) DI Water<br>(8.54%) 2-(2-aminoethoxy)ethanol |
| 1-7 | Citric | | (17.87%) Citric Acid<br>(75.24%) DI Water<br>(6.88%) 2-(2-aminoethoxy)ethanol |

TABLE 1-continued

| Formulation | Carboxylic Acid | Formula | Treatment Composition |
|---|---|---|---|
| 1-8 | Succinic | 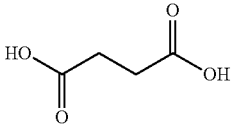 | (94.04%) DI water<br>(5.50%) Succinic acid<br>(0.47%) 2-(2-aminoethoxy)ethanol |
| 1-9 | Succinic + malic | above | (85.04%) DI water<br>(5.08%) Succinic acid<br>(5.06%) Malic Acid<br>(4.82%) 2-(2-aminoethoxy)ethanol |
| 1-10 | Tartaric | 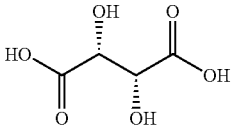 | (78.36%) DI water<br>(13.89%) Tartaric acid<br>(7.75%) 2-(2-aminoethoxy)ethanol |
| 1-12 | Glyoxylic acid monohydrate | 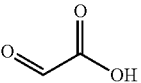 | (8.44%) Glyoxylic Acid<br>(28.4%) Ethanol<br>(60.76%) DI water<br>(2.4%) 2-(2-aminoethoxy)ethanol |

The exemplary treatment compositions of Table 1 may be applied to the hair before or after a color-altering composition, or may be mixed with a color-altering composition for simultaneous application with the color-altering composition.

The following conditioning compositions were prepared by mixing formulations 2b-1 through 2b-8 of Table 2b into the composition of Table 2a.

In Tables 2a-2b, the amounts given are % by weight of the conditioning composition.

TABLE 2a

| Component | wt % |
|---|---|
| WATER | QS |
| PROPYLENE GLYCOL | 3 |
| CETEARYL ALCOHOL | 1 |
| CETEARYL ALCOHOL and BEHENTRIMONIUM METHOSULFATE | 4 |
| GLYCERIN | 0.5 |
| STEARAMIDOPROPYL DIMETHYLAMINE | 0.5 |
| HYDROXYETHYLCELLULOSE | 0.5 |
| QUATERNIUM-91 and CETEARYL ALCOHOL and CETRIMONIUM METHOSULFATE | 0.5 |
| CETRIMONIUM CHLORIDE | 0.55 |
| POLYQUATERNIUM-37 (and) MINERAL OIL (and) PPG-1 TRIDECETH-6 | 0.4 |
| BENZOIC ACID | 0.2 |
| PHENOXYETHANOL | 0.5 |
| 2-(2-AMINOETHOXY)ETHANOL + CARBOXYLIC ACID | Table 2b |

TABLE 2b

| Formulation | 2-(2-AMINOETHOXY)ETHANOL + CARBOXYLIC ACID (pH = 3.5) |
|---|---|
| 2b-1 | 1.474% Oxalic Acid + 1.72% 2-(2-aminoethoxy)ethanol |
| 2b-2 | 1.7% Malonic Acid + 1.72% 2-(2-aminoethoxy)ethanol |
| 2b-3 | 1.933% Succinic Acid + 1.72% 2-(2-aminoethoxy)ethanol |
| 2b-4 | 2.163% Glutaric Acid + 1.72% 2-(2-aminoethoxy)ethanol |
| 2b-5 | 2.195% Malic Acid + 1.72% 2-(2-aminoethoxy)ethanol |
| 2b-6 | 2.457% Tartaric Acid + 1.72% 2-(2-aminoethoxy)ethanol |
| 2b-7 | 1.9% Fumaric Acid + 1.72% 2-(2-aminoethoxy)ethanol |
| 2b-8 | 2.13% Citraconic Acid + 1.72% 2-(2-aminoethoxy)ethanol |

The conditioning compositions prepared by mixing the formulations of Tables 2a and 2b may be applied to the hair after the hair is treated with a treatment composition and/or color-altering composition and/or shape-altering composition, as described herein.

Methods

The following are examples of methods or processes for treating the hair in vitro and in vivo.

Example—Bleaching Process in vitro

A conventional bleach (30 g) and developer (30-60 g) may be mixed with a treatment composition (8 g), applied to the hair, and left on the hair for 50 minutes or more to achieve an equal lift to the bleach standard treated for 50 min. The processing may be done at room temperature. The hair may be rinsed, after which a conditioning composition (0.4 g/g of hair) may be applied to the hair and left for a resting of 10 minutes at room temperature, and then rinsed. The hair may be shampooed and rinsed, and conditioner applied and rinsed.

Example—Bleaching Process In Vivo

A conventional bleach (30 g) and developer (30-60 g) may be mixed with a treatment composition (8 g), applied to the hair, and left on the hair for up to 50 minutes or until desired lift was achieved at room temperature. The hair may be rinsed, after which a conditioning composition (15 g-30 g) may be applied to the hair and left for a resting of 10 minutes at room temperature, and then rinsed. The hair may be shampooed and rinsed, and conditioner applied and rinsed.

Example—Glazing Process In Vivo

A conventional glaze (Shades EQ, 60 g) and processing solution (60 g) may be mixed with a treatment composition (4 g), applied to the hair, and left on the hair for about 20 minutes at room temperature. The hair may be rinsed, after which a conditioning composition (15-30 g) may be applied to the hair and left for a resting of 10 minutes at room temperature, and then rinsed. The hair may be shampooed and rinsed, and conditioner applied and rinsed.

Example—Bleaching and Glazing Process In Vivo

A conventional bleach (30 g) and developer (30-60 g) may be mixed with a treatment composition (8 g), applied to the hair, and left on the hair for about 50 minutes or until desired lift is achieved, at room temperature. The hair may be rinsed and shampooed. A conventional glaze (Shades EQ, 60 g) and processing solution (60 g) may be mixed with a treatment composition (4 g), applied to the hair, and left on the hair for about 20 minutes at room temperature. The hair may be rinsed, after which a conditioning composition (15-30 g) may be applied to the hair and left for a resting of 10 minutes at room temperature, and then rinsed. The hair may be shampooed and rinsed, and conditioner applied and rinsed.

In Vitro Treatment Composition Examples

The following exemplary treatment compositions as set forth in Table 3 were prepared and adjusted to pH 3, except where otherwise indicated. In Table 3, the amounts given are % by weight of the treatment composition, with the balance of each composition being water. The hair treatment selected was a conventional standard bleach including a bleach composition (30 g) and a developer (30-60 g) was mixed with each treatment composition (8 g). The mixture was applied to replicate hair samples, under the recited conditions. The hair samples were then washed and evaluated. All examples were conducted to achieve the same level of lift (lightening level). The time was adjusted accordingly. This allows a direct comparison of the level of damage caused to the hair.

The evaluations of the hair samples treated with the exemplary compositions were compared with the evaluations of the hair samples treated with a standard bleach composition, or with acid or amine alone, or with acid or amine pH adjusted to about pH 3.

Results

Cysteic Acid Data

Since the amount of cysteic acid is an indication of the level of damaged hair, a lower measured concentration indicates that a particular composition provided a protection benefit to the hair fiber. Therefore, the measured concentration of cysteic acid is a marker with respect to the assessment of fiber integrity. An improvement of 10% (% relative change) is typically considered to be statistically significant, such that an increase in the fiber integrity.

A portion of hair samples (swatches) of hair were cut and weighted to approximately 20 mg, hydrolyzed under strong acidic conditions for 16 hours at 110° C. Once hydrolyzed, samples were pH adjusted to approximately 1.7 with a solution of lithium hydroxide and analyzed on a Hitachi amino acid analyzer, Model 8900. Amino acid standards obtained from Sigma Aldrich (Ref AAS18) were utilized to calibrate the instrument and to calculate the concentration of amino acids for each of the treatment conditions. The comparisons shown in Table 3 below show cysteic acid measurements of compositions of Table 3, which were compared to samples treated with only a standard bleach (bleach and developer composition) and to compositions not containing 2-2AEE and at least one carboxylic acid.

Miniature Tensile Tester Data

Hair samples bleached with standard bleach compositions containing treatment compositions containing 2-2AEE were assessed for wet tensile strength using a fiber tensile testing instrument from Dia-Stron known as an MTT (Miniature Tensile Tester). For each sample, 50 fibers were run. From the test, Young's Modulus (elasticity, MPa) and Break Stress (force per unit area required to break the fiber, MPa) were determined. Results of the testing are shown below in Table 4.

Raw Data

TABLE 3

Cysteic Acid Data

| Exemplary Treatment Composition | % Amine/base | moles of Amine/base per 100 g | % Acid | moles Acid per 100 g | pH | Conditions | Cysteic Acid (gAA/ 100 gAA) |
|---|---|---|---|---|---|---|---|
| Standard Bleach | | | | | | 30 V 50 min | 6.4 |
| 2-2AEE + water | 9.46 | 0.090 | — | — | 11.75 | 30 V 50 min | 6.4 |
| Standard Bleach | | | | | | 30 V 50 min | 6.7 |
| Citric Acid + water | — | — | 17.30 | 0.090 | 1.36 | 30 V 75 min | 5.2 |
| Malonic Acid + water | — | — | 9.37 | 0.090 | 1.28 | 30 V 65 min | 5.5 |
| Malic Acid + water | — | — | 12.07 | 0.090 | 1.58 | 30 V 65 min | 5.4 |
| Standard Bleach | | | | | | 30 V 50 min | 6.7 |
| 2-2AEE + Malonic Acid | 9.48 | 0.090 | 13.60 | 0.131 | 3.02 | 30 V 70 min | 5.0 |
| 2-2AEE + Citric Acid | 9.46 | 0.090 | 24.86 | 0.129 | 3.03 | 30 V 80 min | 4.5 |
| Standard Bleach | | | | | | 30 V 50 min | 6.3 |
| 2-2AEE + HCl | 9.46 | 0.090 | 3.97 | 0.109 | 2.94 | 30 V 60 min | 5.8 |
| Standard Bleach | | | | | | 30 V 60 min | 6.6 |
| Malonic Acid + NaOH | 2.63 | 0.066 | 9.37 | 0.090 | 2.99 | 30 V 55 min | 5.8 |
| Citric Acid + NaOH | 2.57 | 0.064 | 17.30 | 0.090 | 2.98 | 30 V 60 min | 5.1 |
| Malic Acid + NaOH | 1.53 | 0.038 | 12.07 | 0.090 | 2.98 | 30 V 60 min | 5.9 |
| Standard Bleach | | | | | | 30 V 50 min | 6.2 |
| Oxalic Acid + water | — | — | 8.10 | 0.090 | 0.61 | 30 V 65 min | 5.0 |
| Standard Bleach | | | | | | 30 V 50 min | 6.5 |
| 2-2AEE + Oxalic Acid | 9.47 | 0.090 | 6.80 | 0.076 | 3.04 | 30 V 60 min | 5.7 |
| Standard Bleach | | | | | | 30 V 50 min | 6.7 |
| Maleic Acid + NaOH | 1.03 | 0.026 | 3.14 | 0.027 | 3.15 | 30 V 50 min | 6.5 |
| 2-2AEE + Maleic Acid | 9.43 | 0.090 | 10.92 | 0.094 | 2.95 | 30 V 50 min | 5.1 |
| Standard Bleach | | | | | | 30 V 50 min | 6.9 |
| Maleic Acid + water | — | — | 10.40 | 0.090 | 0.90 | 30 V 60 min | 5.7 |
| Standard Bleach | | | | | | 30 V 50 min | 6.7 |
| 2-2AEE + Malic Acid | 9.46 | 0.090 | 25.05 | 0.187 | 3.05 | 30 V 85 min | 4.9 |

TABLE 4

MTT Data

| Composition Added to Standard Bleach | % Amine/base | moles of Amine/base per 100 g | % Acid | moles Acid per 100 g | pH | Conditions | MTT Elastic Mod. (Mpa) | MTT Break Stress (Mpa) |
|---|---|---|---|---|---|---|---|---|
| None: Standard Bleach | | | | | | | | |
| 2-2AEE + water | 9.46 | 0.090 | — | — | 11.75 | 30 V 50 min | 927.86 | 111.59 |
| 2-2AEE + HCl | 9.46 | 0.090 | 3.97 | 0.109 | 2.94 | 30 V 60 min | 851.47 | 102.23 |
| Malic Acid + water | — | — | 12.07 | 0.090 | 1.58 | 30 V 65 min | 849.8 | 112.16 |
| Oxalic Acid + water | — | — | 8.10 | 0.090 | 0.61 | 30 V 65 min | 798.83 | 111.96 |
| Malic Acid + NaOH | 1.53 | 0.038 | 12.07 | 0.090 | 2.98 | 30 V 60 min | 955.28 | 107.02 |
| 2-2AEE + Oxalic Acid | 9.47 | 0.090 | 6.80 | 0.076 | 3.04 | 30 V 60 min | 942.41 | 119.91 |
| 2-2AEE + Malic Acid | 9.46 | 0.090 | 25.05 | 0.187 | 3.05 | 30 V 85 min | 1050.96 | 118.45 |
| 2-2AEE + Malonic Acid | 9.48 | 0.090 | 13.60 | 0.131 | 3.02 | 30 V 70 min | 853.57 | 108.13 |
| 2-2AEE + Citric Acid | 9.46 | 0.090 | 24.86 | 0.129 | 3.03 | 30 V 80 min | 785.33 | 102.60 |
| 2-2AEE + Maleic Acid | 9.43 | 0.090 | 10.92 | 0.094 | 2.95 | 30 V 50 min | 832.96 | 112.00 |

Based on the MTT results in Table 4, it is evident that a mixture of bleach with the combination of 2-2AEE and a carboxylic acid provides a large improvement in elastic modulus and break stress compared to bleach alone, as well as to the other examples in the comparison, for an equivalent lift (lightening level). The combination of 2-2AEE and a carboxylic acid therefore provides improved resistance to breakage to hair treated with a mixture comprising the combination.

Strength and Tactile Substance

Hair samples treated with exemplary treatment compositions were tested for tactile substance relative to hair samples treated with 2-2AEE alone, 2-2AEE pH adjusted with hydrochloric acid to pH of about 3, carboxylic acid alone, and carboxylic acid pH adjusted with sodium hydroxide to pH of about 3.

The evaluation for strength (hair that is easy to detangle and comb, having an above average resistance to bend) and tactile substance (smooth surface feel, when pulled maintains elasticity) was carried out visually and by feel by expert evaluators on wet hair sample, and each sample rated for each property. The results are set forth in Table 5 and FIGS. 1-5, where the increase (positive change) and decrease (negative change) are relative to the bleach standard, considered as baseline (0).

TABLE 5

Sensory Data 2-2AEE + Citric Acid (FIG. 1)

| 22AEE + Citric Acid | 22AEE + Water | 22AEE + HCl | 22AEE + Citric Acid | Citric Acid + Water | Citric Acid + NaOH |
|---|---|---|---|---|---|
| Strength | 0 | 0 | −0.5 | 2.5 | 0.5 |
| Tactile Substance | 2 | 1 | 0 | −2.5 | −2 |

Figure 2:
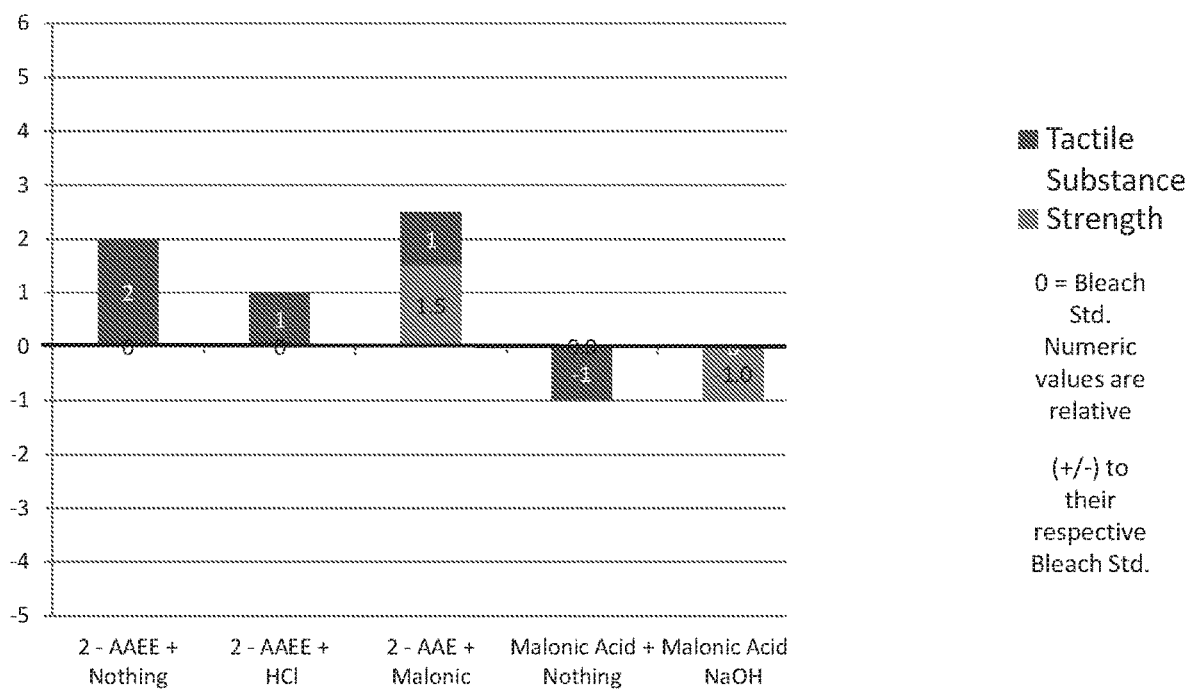

2-2AEE + 2 Malonic Acid (FIG. 2)

| 22AEE + Malonic Acid | 22AEE + Water | 22AEE + HCl | 22AEE + Malonic Acid | Malonic Acid + Nothing | Malonic Acid + NaOH |
|---|---|---|---|---|---|
| Strength | 0 | 0 | 1.5 | 0 | −1 |
| Tactile Substance | 2 | 1 | 1 | −1 | 0 |

TABLE 5-continued

Figure 3:
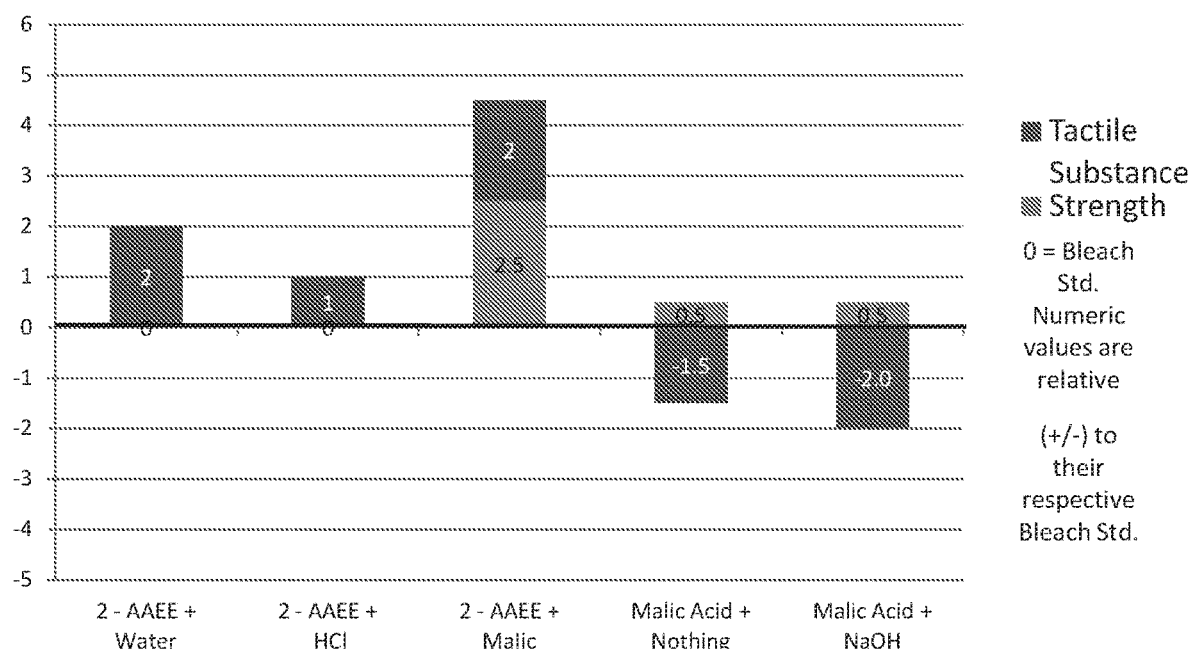

Sensory Data 2-2AEE + Malic Acid (FIG. 3)

| 22AEE + Malic Acid | 22AEE + Water | 22AEE + HCl | 22AEE + Malic Acid | Malic Acid + Nothing | Malic Acid + NaOH |
|---|---|---|---|---|---|
| Strength | 0 | 0 | 2.5 | 0.5 | 0.5 |
| Tactile Substance | 2 | 1 | 2 | −1.5 | −2 |

Figure 4:
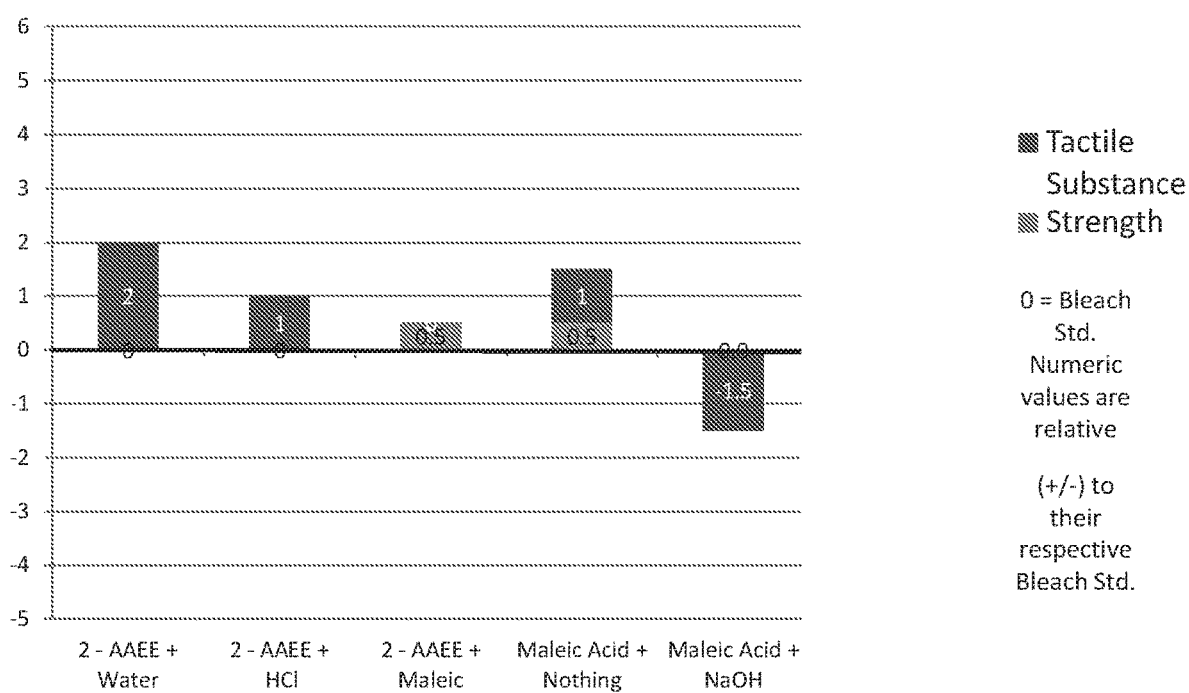

2-2AEE + Maleic Acid (FIG. 4)

| 22AEE + Maleic Acid | 22AEE + Water | 22AEE + HCl | 22AEE + Maleic Acid (ACK) | Maleic Acid + Nothing (ACO) | Maleic Acid + NaOH (ACJ) |
|---|---|---|---|---|---|
| Strength | 0 | 0 | 0.5 | 0.5 | 0 |
| Tactile Substance | 2 | 1 | 0 | 1 | −1.5 |

Figure 5:
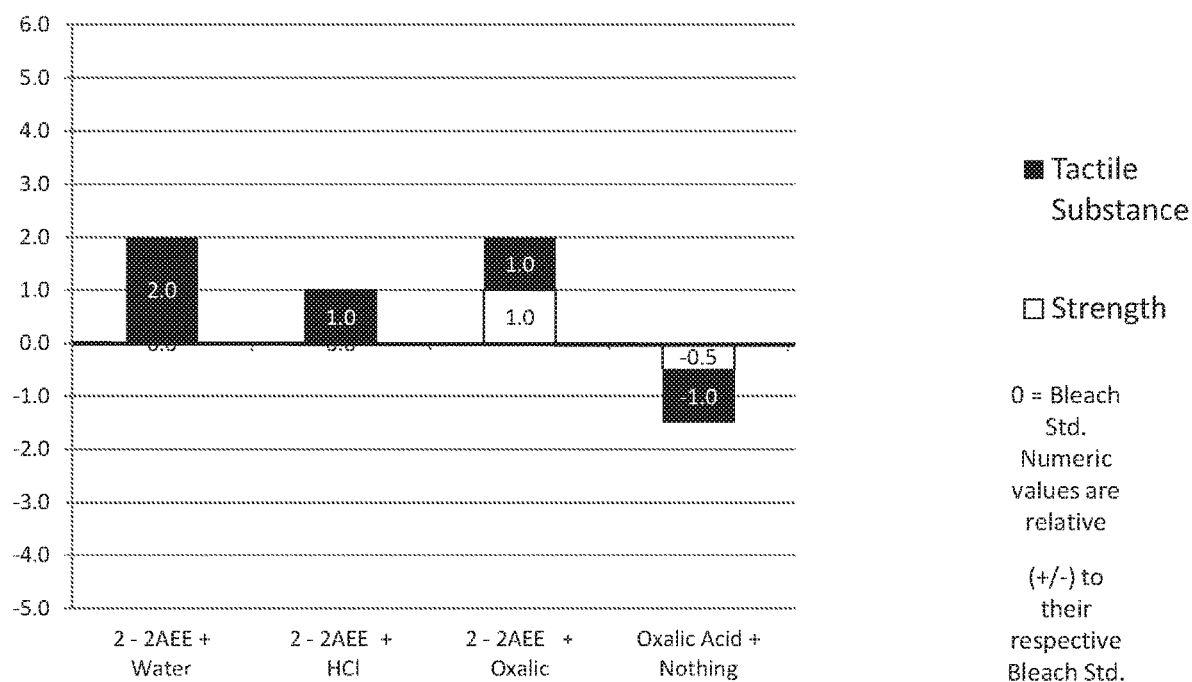

2-2AEE + Oxalic Acid (FIG. 5)

| 22AEE + Oxalic Acid | 22AEE + Water | 22AEE + HCl | 22AEE + Oxalic Acid | Oxalic Acid + Nothing |
|---|---|---|---|---|
| Strength | 0 | 0 | 1 | −0.5 |
| Tactile Substance | 2 | 1 | 1 | −1 |

As shown in Table 5 and FIGS. 1-5, the best combinations of tactile substance and strength resulted from treatment compositions including 2-2AEE and at least one carboxylic acid.

Highlighted Comparisons

For Comparisons 1-2 below, the cysteic acid and MTT data are reproduced from the tables above, but not the sensory data. Note that the sensory conclusions are based on the data shown in the tables from the previous sensory raw data section.

Comparison 1: Oxalic Acid+2-2AEE

TABLE 6

| 2-2AEE + Oxalic Acid Comparison | | | | | | |
|---|---|---|---|---|---|---|
| 2-2AEE + Oxalic Acid | Cysteic Acid Bleach Std (gAA/ 100 gAA) | Cysteic Acid Sample (gAA/ 100 gAA) | Cysteic Acid Absolute Difference | Cysteic Acid % Difference | MTT Elastic Modulus (MPa) | MTT Break Stress (MPa) |
| Bleach Standard | | | | | 730.29 | 105.17 |
| 2-2AEE + Water | 6.4 | 6.4 | 0.0 | 0 | 927.86 | 111.59 |
| 2-2AEE + HCl | 6.3 | 5.8 | 0.5 | 8.26 | 851.47 | 102.23 |
| 2-2AEE + Oxalic | 6.5 | 5.7 | 0.8 | 13.11 | 942.41 | 119.91 |
| Oxalic + Water | 6.2 | 5.0 | 1.2 | 21.43 | 798.38 | 111.96 |

As shown in Table 6, the combination of 2-2AEE and oxalic acid has significantly improved cysteic acid level, more so than the amine alone, amine pH adjusted, or bleach alone. Based on MTT results, this combination of ingredients also showed an improvement in elastic modulus and break stress compared to bleach alone and all the examples in the comparison. Although oxalic acid alone provided cysteic level reduction, it did not provide the internal fiber strength as measured by MTT. The sensory data described above showed that the combination had noticeable improvement in strength and tactile substance over bleach alone, and dramatically improved versus oxalic alone, indicated that this combination of ingredients brings strength to the hair.

Comparison 2: Malic Acid+2-2AEE

TABLE 7

| 2-2AEE + Malic Acid Comparison | | | | | | |
|---|---|---|---|---|---|---|
| 2-2AEE + Malic Acid | Cysteic Acid Bleach Std (gAA/ 100 gAA) | Cysteic Acid Sample (gAA/ 100 gAA) | Cysteic Acid Absolute Difference | Cysteic Acid % Difference | MTT Elastic Modulus (MPa) | MTT Break Stress (MPa) |
| Bleach Standard | N/A | N/A | N/A | N/A | 730.29 | 105.17 |
| 2-2AEE + Water | 6.4 | 6.4 | 0.0 | 0 | 927.86 | 111.59 |
| 2-2AEE + HCl | 6.3 | 5.8 | 0.5 | 8.26 | 851.47 | 102.23 |
| 2-2AEE + Malic | 6.7 | 4.9 | 1.8 | 31.03 | 1050.96 | 118.45 |
| Malic + Water | 6.7 | 5.4 | 1.3 | 21.49 | 849.80 | 112.16 |
| Malic + NaOH | 6.6 | 5.9 | 0.7 | 11.20 | 955.28 | 107.02 |

As shown in Table 7, the combination of 2-2AEE and malic acid has improved cysteic acid level compared to bleach and all the examples in the comparison. In addition, based on the data obtained, this combination showed synergistic effects compared to the amine and acid alone. According to MTT results, this combination of ingredients also showed an increase in elastic modulus and break stress compared to bleach alone and all the examples in the comparison. The sensory data described above showed that the combination had higher strength and tactile substance, when compared to bleach alone and all other bleach combined with additives examples in the data set.

What is claimed is:

1. A hair treatment composition comprising:
   2-(2-aminoethoxy)ethanol; and
   at least one carboxylic acid chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, and glyoxylic acid monohydrate, or combinations thereof.

2. The composition of claim 1, wherein the at least one carboxylic acid is chosen from citric acid, malonic acid, oxalic acid, malic acid, glutaric acid, glycolic acid, succinic acid, adipic acid, tartaric acid, sebacic acid, glyoxylic acid monohydrate, or combinations thereof.

3. The composition of claim 1, wherein the at least one carboxylic acid is chosen from maleic acid, citraconic acid, fumaric acid, benzoic acid, or combinations thereof.

4. The composition of claim 1, wherein the at least one carboxylic acid is chosen from oxalic acid, malic acid, or combinations thereof.

5. The composition of claim 1, wherein the 2-(2-aminoethoxy)ethanol is present in an amount up to about 15% by weight, relative to the total weight of the composition.

6. The composition of claim 1, wherein the 2-(2-aminoethoxy)ethanol is present in an amount up to about 3% by weight, relative to the total weight of the composition.

7. The composition of claim 1, wherein the at least one carboxylic acid is present in an amount up to about 30% by weight, relative to the total weight of the composition.

8. The composition of claim 1, wherein the at least one carboxylic acid is present in an amount up to about 5% by weight, relative to the total weight of the composition.

9. The composition of claim 1, further comprising at least one additive chosen from surfactants, solvents, conditioning agents, or combinations thereof.

10. The composition of claim 9, wherein the solvents are chosen from water, cosmetically acceptable organic solvents, or combinations thereof.

11. A hair treatment system comprising:
    (a) a hair treatment composition comprising:
       2-(2-aminoethoxy)ethanol;
       at least one carboxylic acid chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, or combinations thereof; and
       at least one solvent; and
    (b) a hair conditioning composition comprising:
       2-(2-aminoethoxy)ethanol;
       at least one carboxylic acid chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, or combinations thereof; and
       at least one additive.

12. The hair treatment system of claim 11, wherein the at least one carboxylic acid present in the hair treatment composition and/or the hair conditioning composition is independently chosen from citric acid, malonic acid, oxalic acid, malic acid, glutaric acid, glycolic acid, succinic acid, adipic acid, tartaric acid, sebacic acid, glyoxylic acid monohydrate, or combinations thereof.

13. The hair treatment system of claim 11, wherein the at least one carboxylic acid present in the hair treatment composition and/or the hair conditioning composition is independently chosen from maleic acid, citraconic acid, fumaric acid, benzoic acid, or combinations thereof.

14. The hair treatment system of claim 11, wherein the at least one carboxylic acid present in the hair treatment composition and/or the hair conditioning composition is independently chosen from oxalic acid, malic acid, maleic acid, or combinations thereof.

15. The hair treatment system of claim 11, further comprising at least one composition or agent for coloring or shaping the hair.

16. The hair treatment system of claim 15, wherein the composition for coloring or shaping the hair comprises the hair treatment composition.

17. The hair treatment system of claim 11, wherein the agent for coloring the hair is chosen from bleaching agents, colorant compounds, or combinations thereof, and/or the agent for shaping the hair is chosen from agents for straightening, relaxing, or permanent waving the hair.

18. The hair treatment system of claim 17, wherein:
the bleaching agents are chosen from peroxides, persulfates, perborates, percarbonates, peracids, bromates, their salts, or mixtures thereof; and
the colorant compounds are chosen from oxidation dyes, direct dyes, pigments, or mixtures thereof.

19. A method of treating hair, the method comprising:
applying to the hair a hair treatment composition comprising:
2-(2-aminoethoxy)ethanol;
at least one carboxylic acid chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, or combinations thereof; and
at least one solvent.

20. The method of claim 19, further comprising applying to the hair a hair conditioning composition, the hair conditioning composition comprising:
2-(2-aminoethoxy)ethanol;
at least one carboxylic acid chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, or combinations thereof; and
at least one additive.

21. The method of claim 20, optionally comprising a step of shampooing and/or rinsing the hair after applying the hair treatment composition to the hair, and/or after applying to the hair conditioning composition to the hair.

22. The method of claim 19, wherein the hair treatment composition further comprises at least one composition or agent for coloring or shaping the hair.

23. The method of claim 22, wherein the at least one composition or agent for coloring or shaping the hair is chosen from bleaching agents, colorant compounds, or combinations thereof.

24. The method of claim 23, wherein:
the bleaching agents are chosen from peroxides, persulfates, perborates, percarbonates, peracids, bromates, their salts, or mixtures thereof; and
the colorant compounds are chosen from oxidation dyes, direct dyes, pigments, or mixtures thereof.

25. The method of claim 22, wherein the at least one composition or agent for coloring or shaping the hair is mixed with the hair treatment composition prior to application to the hair.

26. The method of claim 25, wherein the mixing of the at least one composition or agent for coloring or shaping the hair occurs less than about one hour prior to application of the mixture to the hair.

27. The method of claim 19, further comprising applying to the hair a color-altering composition, the color-altering composition comprising at least one bleaching agent, at least one colorant compound, or combinations thereof, before, after, or simultaneously with the step of applying the hair treatment composition.

28. The method of claim 19, wherein the hair treatment composition is applied to the hair following a reducing step of a hair-shaping process, further comprising optionally leaving the hair treatment composition on the hair for a processing time ranging from about 5 minutes to about 20 minutes, and optionally blotting or rinsing the hair after the optional processing time.

29. A multi-compartment kit for altering the color or shape of the hair, the kit comprising:
(a) at least one first compartment comprising a hair treatment composition, the hair treatment composition comprising:
2-(2-aminoethoxy)ethanol;
at least one carboxylic acid chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, or combinations thereof; and
at least one solvent;
(b) at least one second compartment containing a hair conditioning composition, the hair conditioning composition comprising:
2-(2-aminoethoxy)ethanol;
at least one carboxylic acid chosen from maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, or combinations thereof; and
at least one additive; and
(c) optionally, at least one additional compartment comprising at least one agent for coloring or shaping the hair.

* * * * *